(12) United States Patent
Han et al.

(10) Patent No.: US 12,397,084 B2
(45) Date of Patent: Aug. 26, 2025

(54) SYNTHETIC HYDROGEL CARRIERS FOR MUSCLE REPAIR

(71) Applicant: Georgia Tech Research Corporation, Atlanta, GA (US)

(72) Inventors: Woojin Han, Atlanta, GA (US); Andres J. Garcia, Atlanta, GA (US); Young C. Jang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1119 days.

(21) Appl. No.: 17/263,021

(22) PCT Filed: Jul. 23, 2019

(86) PCT No.: PCT/US2019/042953
§ 371 (c)(1),
(2) Date: Jan. 25, 2021

(87) PCT Pub. No.: WO2020/023462
PCT Pub. Date: Jan. 30, 2020

(65) Prior Publication Data
US 2021/0236686 A1   Aug. 5, 2021

Related U.S. Application Data

(60) Provisional application No. 62/702,039, filed on Jul. 23, 2018.

(51) Int. Cl.
*A61L 26/00* (2006.01)
*A61J 1/20* (2006.01)
*A61M 37/00* (2006.01)

(52) U.S. Cl.
CPC ........... *A61L 26/008* (2013.01); *A61J 1/2096* (2013.01); *A61L 26/0047* (2013.01); *A61M 37/0015* (2013.01); *A61L 2300/412* (2013.01); *A61L 2430/30* (2013.01); *A61M 2037/0023* (2013.01); *A61M 2037/0061* (2013.01)

(58) Field of Classification Search
CPC ............... A61L 26/008; A61L 26/0047; A61L 2300/412; A61L 2430/30; A61J 1/2096; A61M 37/0015; A61M 2037/0023; A61M 2037/0061; A61K 35/34; A61K 38/18; A61K 47/36; A61K 9/0024; A61P 21/00
See application file for complete search history.

(56) References Cited

U.S. PATENT DOCUMENTS 8,067,237 B2 * 11/2011 Mooney ................. A61L 27/58
435/402
9,169,309 B2  10/2015 Jeong
9,381,217 B2   7/2016 Garcia et al.

FOREIGN PATENT DOCUMENTS

WO   2018/165565   9/2018

OTHER PUBLICATIONS

Phelps et al., "Maleimide cross-linked bioactive PEG hydrogels exhibit improved reaction kinetics and cross-linking for cell encapsulation and in-situ delivery", Advanced Materials, 2012, 64-70 (Year: 2012).*
Gilbert et al. "Substrate Elasticity Regulates Skeletal Muscle Stem Cell Self-Renewal in Culture", Science, 2010, 1078-1081 (Year: 2010).*
Phelps et al. "Maleimide Cross-Linked Bioactive PEG Hydrogel Exhibits Improved Reaction Kinetics and Cross-Linking for Cell Encapsulation and In Situ Delivery", Advanced Materials, 2012, 64-70 (Year: 2012).*
Lee et al. "Drug Delivery using microneedle patches: not just for skin", Expert Opinion on Drug Delivery, 2018, pp. 541-543 (Year: 2018).*
Laumonier et al, Journal of Experimental Orthopaedics, 2016, 3:15, 1-9]. (Year: 2016).*
Karalaki et al [in vivo, 2009, 23, 779-796] (Year: 2009).*
Musaro [Advances in Biology, 2014, article ID 612471, 1-16] (Year: 2014).*
He et al, Molecules, 2019, 24, 1855, 1-34 (Year: 2019).*
Lu et al, International Journal of Molecular Sciences, 2016, 17, 561, 1-22 (Year: 2016).*
Chen et al. Adv. Drug Deliv. Rev. 65: 1357-1369, 2013. (Year: 2013).*
International Search Report and Written Opinion dated Oct. 29, 2019, from International Application No. PCT/US2019/042953, 11 pages.
Enemchukwu, N. et al. "Synthetic matrices reveal contributions of ECM biophysical and biochemical properties to epithelial morphogenesis", The Journal of Cell Biology, vol. 212, No. 1, 113-124.

* cited by examiner

*Primary Examiner* — Sudhakar Katakam
(74) *Attorney, Agent, or Firm* — Meunier Carlin & Curfman LLC

(57) ABSTRACT

Disclosed herein are hydrogels that can be loaded with myogenic agents, for instance muscle stem cells (MuSCs)/satellite cells, pro-myogenic factors, and combinations thereof. The hydrogels can be contacted with damaged muscle tissue, thereby facilitating muscle growth and repair. Further provided are methods of repairing muscle tissue in a patient in need thereof, said methods comprising contacting the muscle tissue with a composition comprising the hydrogel. Also provided herein are kits comprising the hydrogel composition and a substrate comprising at least one microneedle.

19 Claims, 16 Drawing Sheets
Specification includes a Sequence Listing.

SYNTHETIC HYDROGEL CARRIERS FOR MUSCLE REPAIR

CROSS REFERENCE TO RELATED APPLICATION

This application claims the benefit of U.S. Provisional Application 62/702,039, filed on Jul. 23, 2018, the contents of which are hereby incorporated in its entirety.

STATEMENT OF GOVERNMENT SUPPORT

This invention was made with government support under RO1 AR062920, R21 AR072287, and F32HL140821, awarded by the National Institutes of Health. The government has certain rights in this invention.

FIELD OF THE INVENTION

The invention is directed to synthetic hydrogels that are loaded with one or more myogenic agents. The hydrogels may be contacted with an injured muscle tissue in order to facilitate tissue regeneration.

BACKGROUND

Skeletal muscle generates force to enable movement and support vital functions such as deglutition and respiration. Although healthy muscle exhibits remarkable adaptive and regenerative capacities, its function declines with comorbidity of severe physical trauma, aging, and disease. Inadequate regeneration of muscle begets debilitating consequences, including long-term disabilities and reduced quality of life. Current clinical interventions for muscle trauma entail muscle flap transfer and surgical suture, but these treatments alone do not completely regenerate the damaged muscle. Clinical strategies that effectively regenerate traumatically injured muscle in comorbidity with aging and muscle pathology currently do not exist and are in great critical need.

The diaphragm is a thin skeletal muscle that sits at the base of the chest and separates the abdomen from the chest. During inhalation, the diaphragm contracts and flattens, creating a vacuum effect that pulls air into the lungs. As the diaphragm relaxes the air is pushed out of lungs. Damage to the diaphragm, whether through trauma or disease, can lead to difficulties breathing, potentially leading to death if not corrected.

Duchenne muscular dystrophy ("DMD") is caused by a defect in the expression of the protein dystrophin. Disease onset can be documented at birth with elevated creatine kinase levels, and significant motor deficits may be present in the first year of life. By the age of seven or eight, most patients with DMD have an increasingly labored gait and are losing the ability to rise from the floor and climb stairs; by ages 10 to 14, most are wheelchair-dependent. DMD is uniformly fatal; affected individuals typically die of respiratory and/or cardiac failure in their late teens or early 20s. Current therapies for DMD include glucocorticoids, which are associated with numerous side effects including weight gain, behavioral changes, pubertal changes, osteoporosis, Cushingoid facies, growth inhibition, and cataracts.

Muscle satellite cells (MuSCs) are muscle-resident stem cells that play an indispensable role in myogenesis, and their function centrally dictates the regenerative capacity of muscle in the context of injury, aging, and disease. Upon injury, quiescent MuSCs (Pax7$^+$/MyoD$^-$) activate to give rise to proliferating myoblasts (MyoD$^+$) that undergo myogenic differentiation or fusion with existing myofibers. Importantly, asymmetric division of MuSCs maintains muscle homeostasis, where this process is critical for regeneration of damaged myofibers and repopulation of the stem cell reservoir through self-renewal for ensuing regenerative needs. However, the intrinsic function and quantity of MuSCs decline with aging and neuromuscular diseases, such as DMD, and contribute to the diminished regenerative potential of muscle. For example, one mechanism that causes age-associated decline in MuSC function and number is that MuSCs lose the ability to asymmetrically divide from abnormal JAK-STAT and p38 signaling and undergo cellular senescence from elevated p16$^{INK4A}$. In DMD, dystrophin-deficient MuSCs exhibit impaired mitosis and loss of asymmetric division. Dysregulation of MuSC function ultimately results in depletion of the MuSC reservoir and defective muscle regenerative potential. The regenerative potential further diminishes upon traumatic muscle injuries, such as bone-muscle polytrauma, laceration, crush, and severe burn, where MuSCs undergo concurrent activation and cell death.

Transplantation of MuSCs into injured, aging, and dystrophic muscles results in engraftment and repopulation of the quiescent MuSC pool. Although approaches aimed to replenish functional MuSCs in traumatically injured muscles in the comorbid context of aging or chronic pathology may be an effective strategy to boost degenerating muscle function, successful and translatable approaches to transplant MuSCs in traumatically injured aged or pathologic muscles have not yet been developed. If a successful strategy for MuSC could be achieved, it would have significant potential for administering MuSCs as a cellular source for stem cell therapy for muscle injury, sarcopenia, and muscular dystrophy. However, previous proof-of-principle transplantation experiments have been conducted on skeletal muscles that were cardiotoxin/notexin/BaCl$_2$-injured, irradiated, and/or immunodeficient, limiting their clinical translatability. Direct injections of MuSC are not always feasible in the case of traumatic injuries and diseases exhibiting a severe loss in tissue integrity. Furthermore, direct delivery of cells via injection has challenges at the translational level, including massive donor cell death and cellular dispersion, severely limiting its therapeutic potential. Indeed, only 1-20% of the transplanted cells survive in the host tissue due to the harsh inflammatory environment, and the surviving donor cells exhibit limited function. It is also important to note that cell delivery via injection may not always be applicable in traumatic injuries, where the structural integrity of the muscle is often severely compromised to receive an injection. To address these limitations, naturally-derived biomaterials, such as decellularized matrix, collagen, hyaluronic acid, fibrin, and alginate hydrogels have been utilized to facilitate the delivery of myogenic cells to the muscle. However, naturally-derived materials are susceptible to lot-to-lot variability, potential pathogen transfer, and difficulty in controlling the material's microstructure, mechanical properties, and degradability—these limitations hinder their translatability, wide applicability, and systematic investigation of material-MuSC interactions to improve engraftment efficacy. Furthermore, previous studies used non-quiescent myoblasts that had been expanded in vitro, and thus knowledge on how the biochemical and biophysical properties of these materials impact quiescent MuSC activities is limited.

Wingless-type MMTV Integrated 7a (Wnt7a) protein, a ligand for Frizzled (Fzd) receptors, functions as a potent mediator of muscle growth and repair. Notably, Wnt7a induces myofiber hypertrophy through the Akt/mTOR protein synthesis pathway, promotes symmetric expansion, and migration of MuSCs through the planar cell polarity pathway involving Dishevelled 2 (Dvl2) and the small GTPase Rac1. Furthermore, pre-treatment of MuSCs with Wnt7a significantly enhances MuSC dispersion and engraftment upon cellular transplantation. In a rodent model of Duchenne muscular dystrophy, administration of recombinant human Wnt7a into tibialis anterior muscles significantly promotes MuSC expansion, myofiber hypertrophy, and muscle strength, suggesting that Wnt7a serves as an effective pro-myogenic factor for stimulating muscle repair. Although Wnt7a treatment may also enhance local muscle regeneration in the contexts of injuries and diseases, direct injection of Wnt7a can be difficult in muscle conditions with a severe loss of integrity. Therefore, there is a need for a delivery vehicle that enables controlled administration of therapeutics to the injured or pathologic muscles where direct injections may not be applicable.

There remains a need for improved carriers for delivering therapeutic agents to injured muscle tissue. There remains a need for improved methods of delivering therapeutically effective amounts of muscle cells and myogenic proteins to injured muscle tissue. There remains a need for improved methods of repaired damaged diaphragm tissue. There remains a need for improved treatments of muscular dystrophy, including Duchenne's muscular dystrophy.

SUMMARY

Disclosed herein are hydrogels that can be loaded with myogenic agents, for instance muscle stem cells (MuSCs)/satellite cells, pro-myogenic factors, and combinations thereof. The hydrogels can be contacted with damaged muscle tissue, thereby facilitating muscle growth and repair. The details of one or more embodiments are set forth in the descriptions below. Other features, objects, and advantages will be apparent from the description and from the claims.

Quantification of bioluminescence over time. Mean±SEM. n=8 per condition. * p<0.05,  p<0.01, ** p<0.0001 vs hydrogel-free via Tukey's test within time. ++p<0.01 vs 6% PEG-4MAL via Tukey's test within time. *p<0.05 for interactions, xx p<0.01 for biomaterials effect, ###p<0.001 for time effect via two-way repeated measures ANOVA. (D) Quantification of area under the bioluminescence curve (AUC). Mean±SEM. n=8 per condition. * p<0.05 vs hydrogel-free via 1-way ANOVA with Tukey's test. (E) Representative cross-sections of TA muscles treated with cell-laden 3% 20 kDa PEG-4MAL, 6% 20 kDa PEG-4MAL, or media on day 28 post-transplantation. Scale bar: 50 μm. (F) Quantification of GFP$^+$ fibers per mm$^2$. n=8 per condition. * p<0.05 vs all groups via Kruskal-Wallis with Dunn's test. (G) Representative cross-sections of TA muscles treated with cell-laden 3% 20 kDa PEG-4MAL functionalized with RGD or RDG peptides at day 28 post-transplantation. 12,500 MuSCs/TA. Scale bar: 50 μm. (H) Quantification of GFP$^+$ fibers per mm$^2$. n=6 per condition. * p<0.05 via two-tailed Mann-Whitney U test. (I) Representative IVIS images of MuSC-transplanted mdx-4CV mice. TAs were cryo-injured, and 20,000 MuSCs were delivered to the injured TA muscles in either PEG-4MAL hydrogel (left) or 2.7 mg·ml$^{-1}$ collagen gel (right). (J) Quantification of bioluminescence over time. Mean±SEM. n=5 per condition. ++p<0.01 within time via Sidak's test. * p<0.05 for interactions and biomaterials effect via two-way repeated-measures ANOVA. ###p<0.05 for time effect via two-way repeated-measures ANOVA. (K) Quantification of area under the bioluminescence curve (AUC). n=8 per condition. * p<0.05 via two-tailed paired t-test. (L) Representative cross-sections of TA muscles treated with 50,000 MuSCs in either PEG-4MAL or 2.7 mg·ml$^{-1}$ collagen gel. Scale bar: 100 μm. (M) Quantification of engrafted GFP$^+$ fibers per mm$^2$. n=8 per condition. ** p<0.01 via two-tailed Wilcoxon matched-pairs signed rank test.

Figure 6:
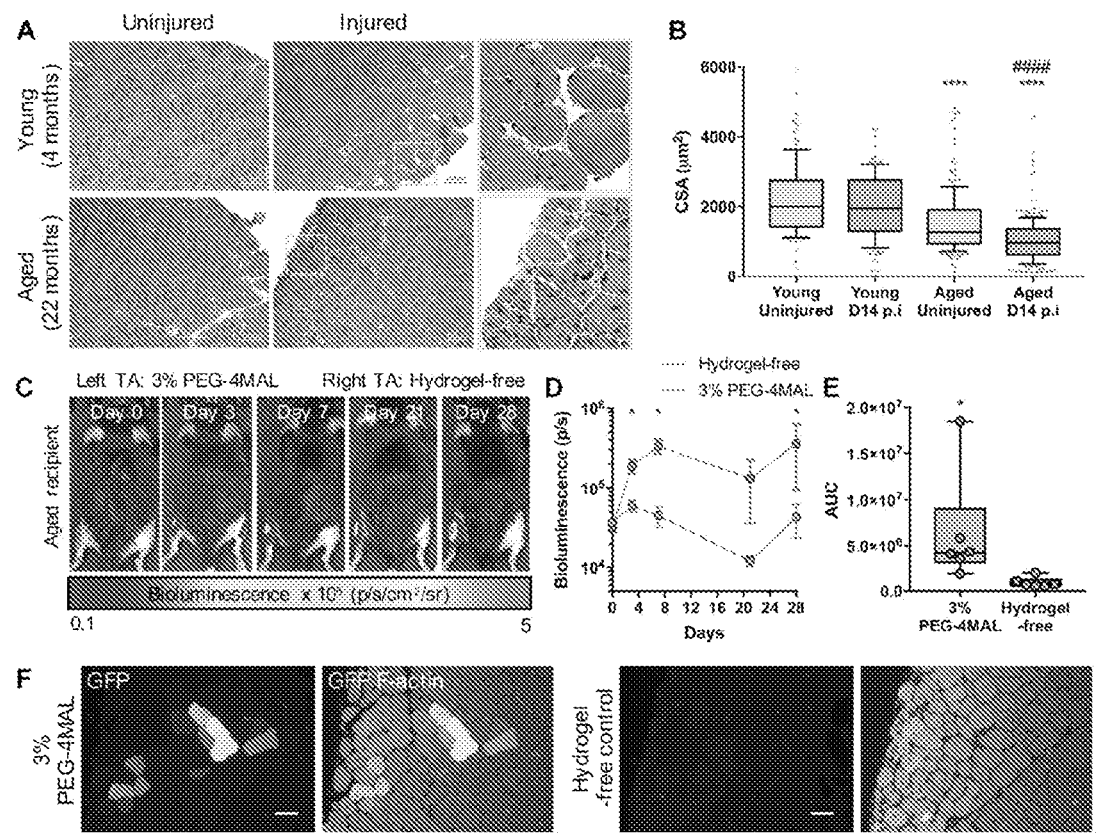

FIG. 6. Synthetic matrix enhances engraftment in aged muscle trauma. (A) H&E images of young (4 months) and aged (22 months) TA muscles. Muscles were cryo-injured and endogenous regeneration was assessed on day 14. (B) Quantification of cross-sectional area (CSA). Box-whiskers plot with 10-90 percentile whiskers. ≥138 fibers were measured. p.i: post-injury. **** p<0.0001 vs young uninjured and young D14 p.i.; ####p<0.0001 vs aged uninjured via 1-way ANOVA with Dunn's test. (C) Representative IVIS images of aged mice (23 months). TAs were cryo-injured and 20,000 MuSCs encapsulated in PEG-4MAL hydrogel (left) or suspended in media (right) were transplanted. (D) Quantification of bioluminescence over time. Mean±SEM. n=6 per condition. * p<0.05 via two-tailed Wilcoxon matched-pairs signed rank test within time. (E) Quantification of area under the bioluminescence curve (AUC). n=6 per condition. * p<0.05 via two-tailed Wilcoxon matched-pairs signed rank test. (F) Cross-sections of TA muscles at day 28 post-transplantation. Scale bar: 50 μm.

Figure 7:
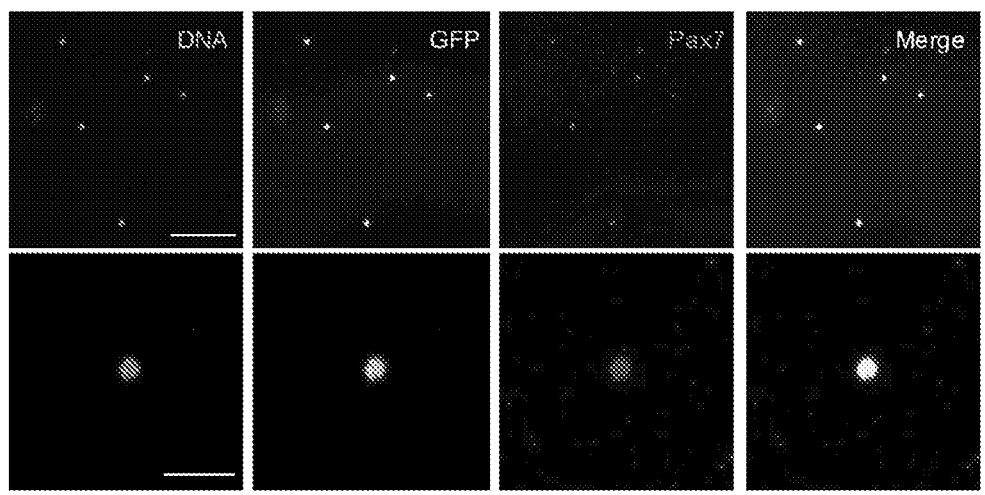

FIG. 7. Isolated primary MuSCs are Pax7$^+$. Freshly isolated cells were encapsulated in PEG-4MAL hydrogel and immediately fixed and stained. Top row scale bar: 100 μm. Bottom row scale bar: 10 μm.

Figure 8:
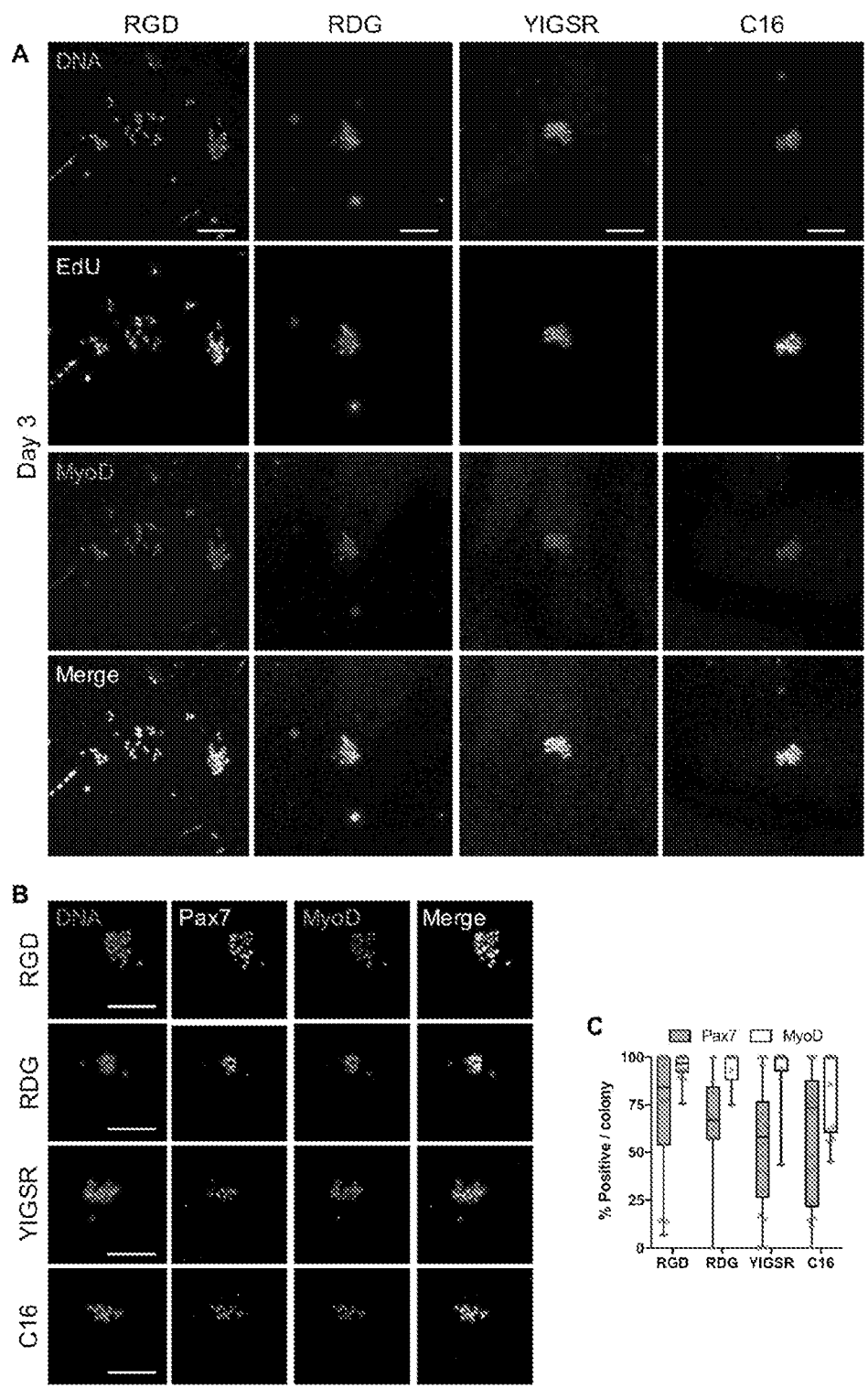

FIG. 8. RGD-presenting hydrogels promote MuSC activation and proliferation. (A) Representative z-projections myogenic colonies formed in hydrogels presenting synthetic cell adhesive peptides. Day 3. Scale bar: 100 μm. (B) MuSCs encapsulated and cultured in PEG-4MAL hydrogels become activated (Pax7$^+$/MyoD$^+$) by 72 hours post-encapsulation in culture. (C) Quantification of Pax7$^+$ and MyoD$^+$ cells. n=9-18. p=0.28 (Pax7) and p=0.69 (MyoD) Kruskal-Wallis test.

Figure 9:
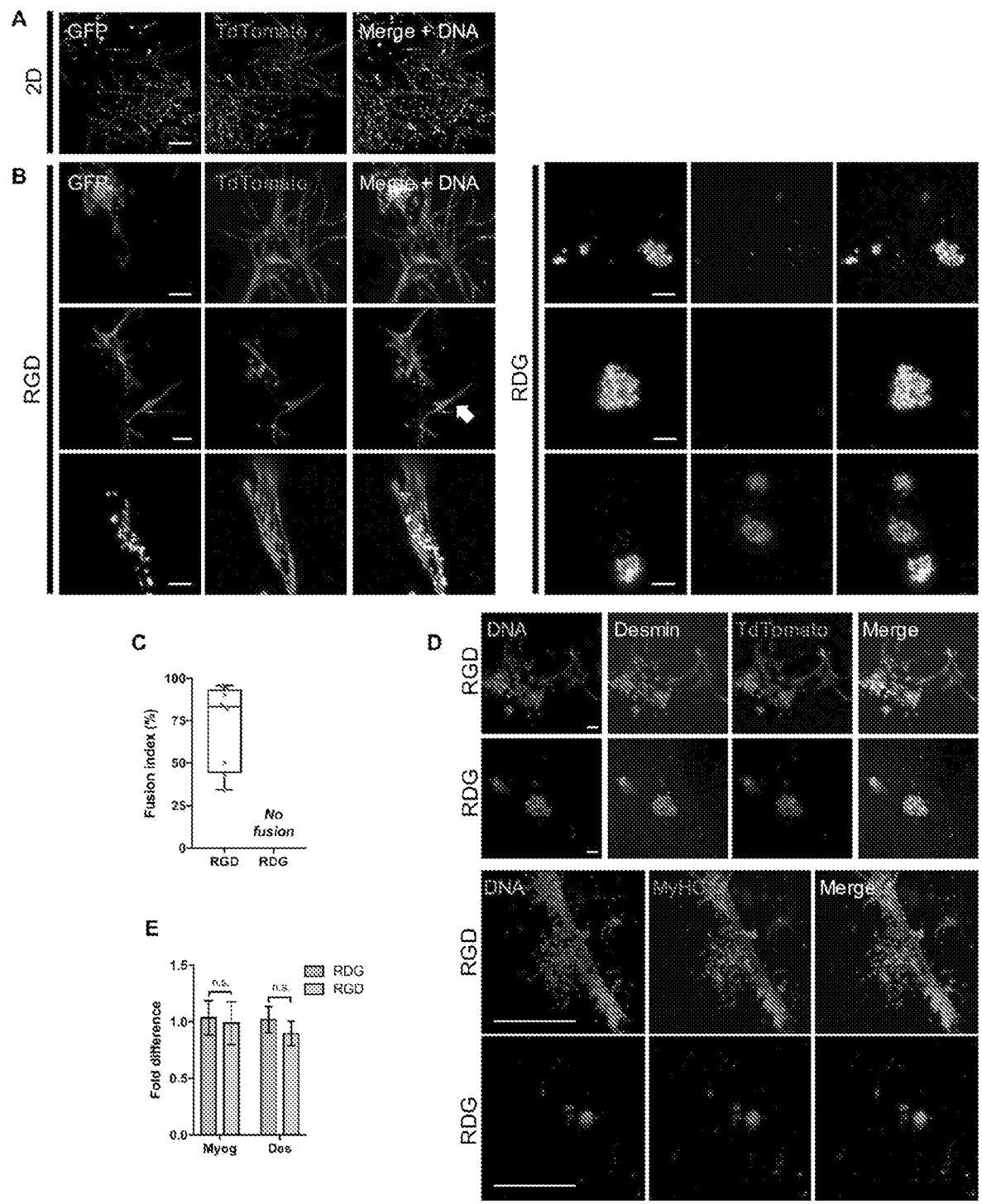

FIG. 9. RGD-presenting hydrogels promote MuSC differentiation. (A) Freshly isolated GFP$^+$ and TdTomato$^+$ MuSCs were seeded (1:1) collagen/laminin-coated tissue culture plastic to demonstrate fusion through co-expression of GFP and TdTomato. Scale bar: 200 μm. (B) Freshly isolated GFP$^+$ and TdTomato$^+$ MuSCs were seeded (1:1) in PEG-4MAL hydrogels functionalized with RGD or RDG. Cells cultured in RGD-functionalized hydrogels fuse (arrow) and become more elongated compared to the cells cultured in RDG-functionalized hydrogels. (C) Quantification of fusion index (%). n=8. p<0.0001 via unpaired two-tailed t-test. (D) Cells cultured in both RGD- and RDG-functionalized hydrogels stain positive for desmin and myosin heavy chain (MyHC). Cells were cultured in growth media for 6 days, then in differentiation media for 4 days. Scale bars: 100 μm (Desmin), 500 μm (MyHC). (E) Quantification of myogenin and desmin gene expression. n=4-5. n.s. p>0.05. Mean±SEM.

Figure 10:
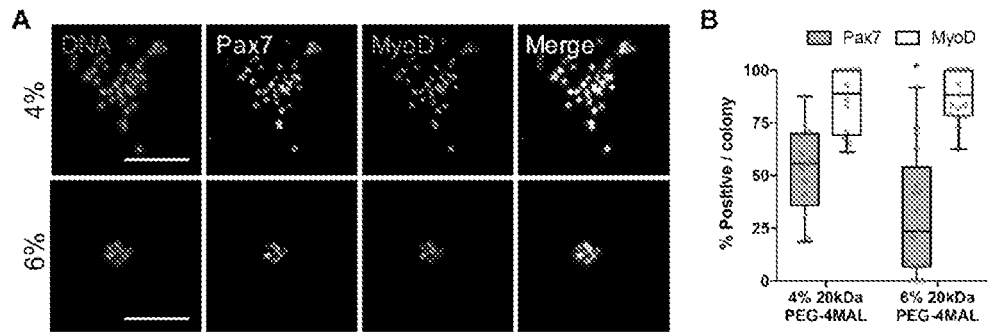

FIG. 10. Pax7/MyoD Expression of MuSCs in 4% and 6% 20 kDa PEG-4MAL hydrogels. (A) MuSCs encapsulated and cultured in PEG-4MAL hydrogels become activated (MyoD$^+$) by 76 hours post-encapsulation in culture. Scale bar: 50 μm. (B) Quantification of Pax7$^+$ and MyoD$^+$ cells. n=13-17. * p<0.05 via unpaired t-test.

Figure 11:
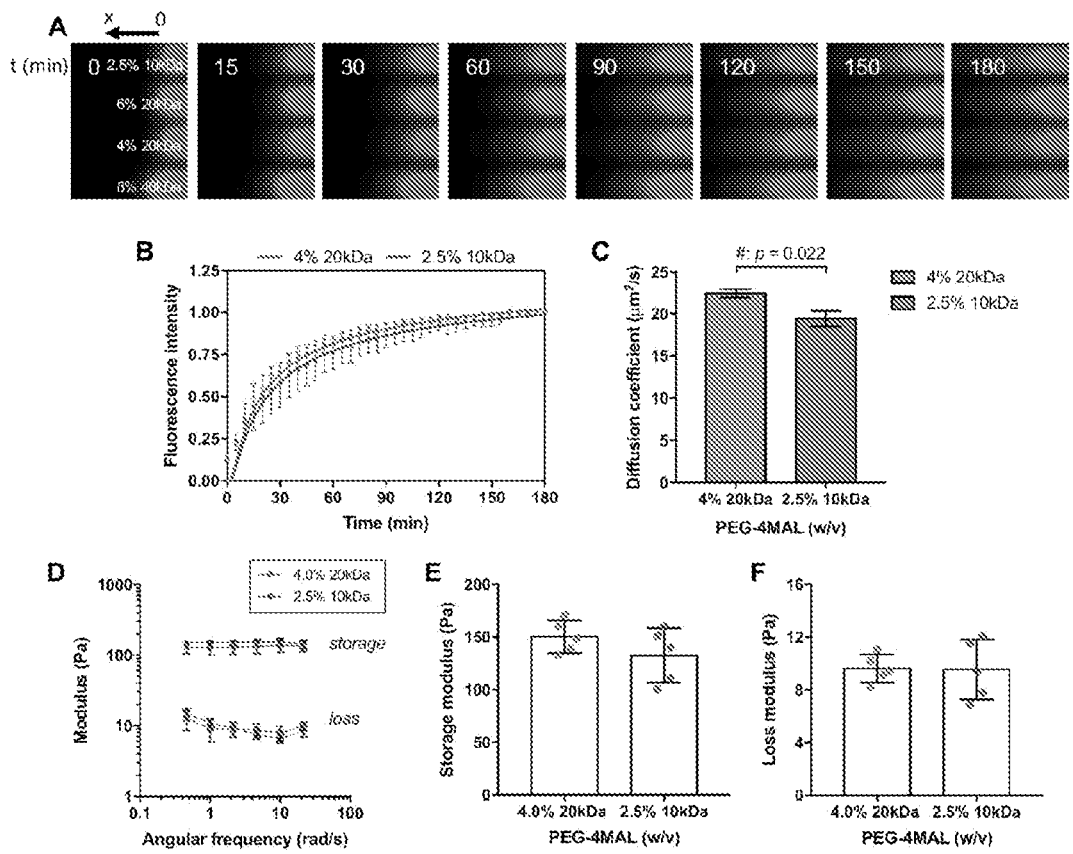

FIG. 11. One-dimensional diffusion assay in PEG-4MAL hydrogels. (A) Representative micrographs of Alexa-555-labeled α-bungartoxin (8 kDa) diffusing into PEG-4MAL gels over time. (B) Quantification of intensity. The solution of Fick's second law was fitted through the data to determine the diffusion coefficients. n=5. Mean±SEM. (C) Diffusion coefficients determined from curve fitting. n=5. Mean±SEM. (D-F) Rheological assessments of 4% 20 kDa and 2.5% 10 kDa PEG-4MAL hydrogels. n=5. Mean±SD. #p<0.05 via unpaired two-tailed t-test.

Figure 12:
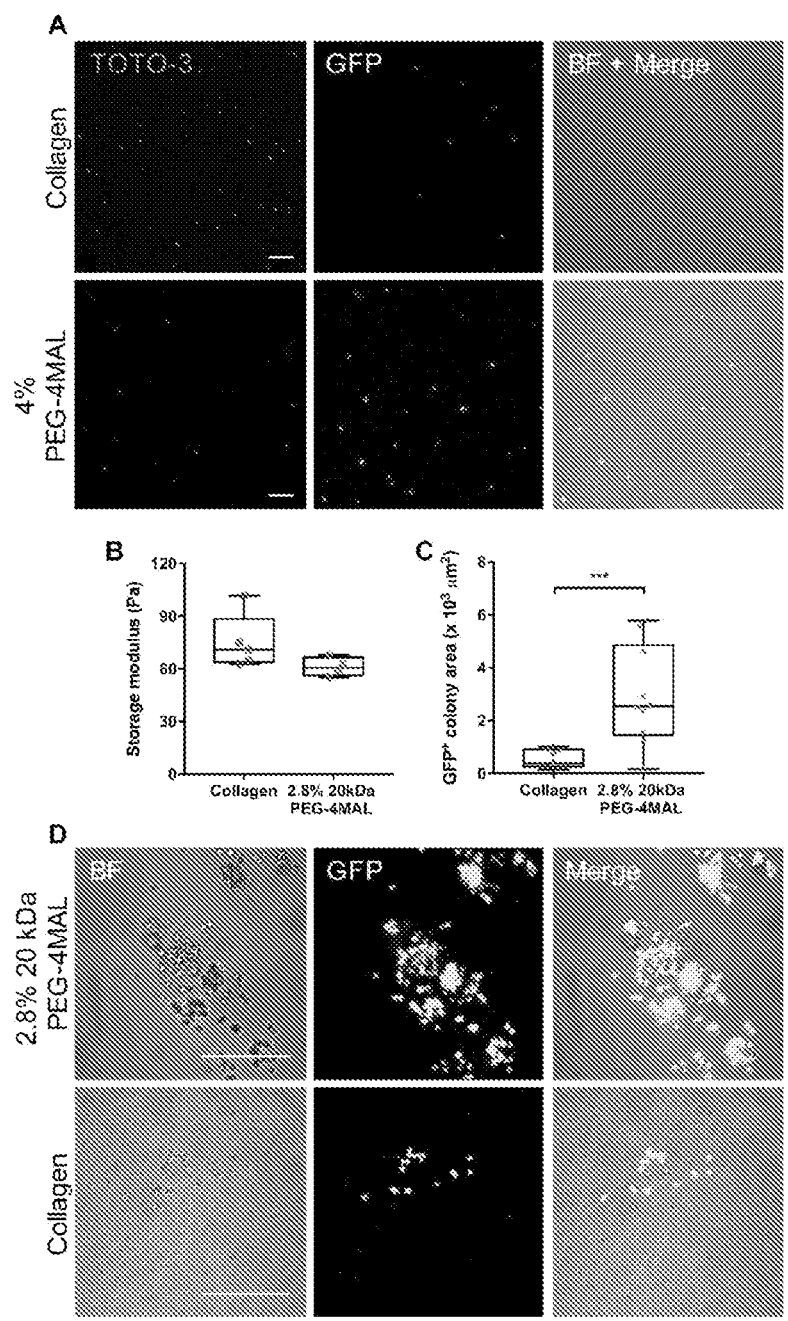

FIG. 12 Synthetic matrix supports higher MuSC proliferation potential than collagen gel. (A) Representative z-projections of GFP$^+$ MuSCs 1-day post-encapsulation in 4% PEG-4MAL hydrogel and 2.7 mg·ml$^{-1}$ collagen gel. Scale bar: 100 μm. (B) Storage modulus of 2.8% PEG-4MAL hydrogel and 2.7 mg·ml$^{-1}$ collagen gel. n=4-5. p=0.14 via unpaired t-test. (C) Quantification of GFP$^+$ myogenic colony area in 4% PEG-4MAL hydrogel and 2.7 mg·ml$^{-1}$ collagen gel. n=10. *** p<0.001 via unpaired two-tailed t-test. (D) Representative z-projections of GFP$^+$ MuSCs 3-days post-encapsulation in 2.8% PEG-4MAL hydrogel and 2.7 mg·ml$^{-1}$ collagen gel. Scale bar: 100 μm.

Figure 13:
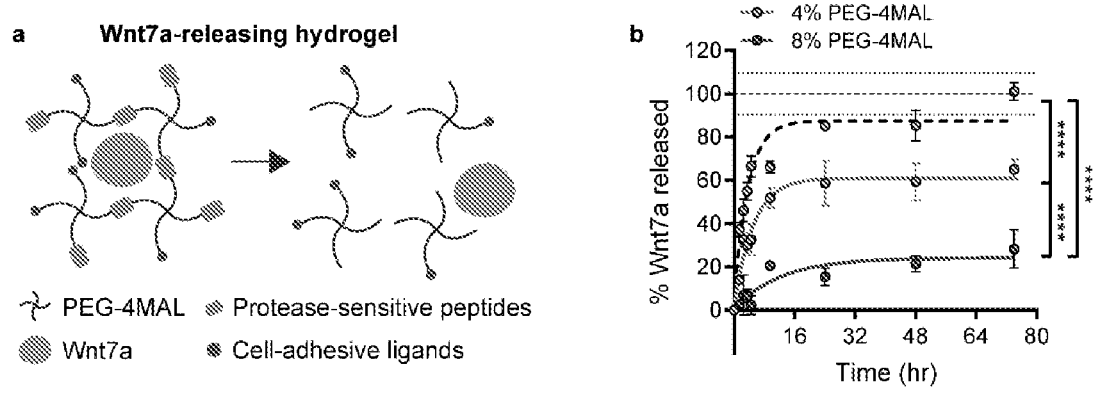

FIG. 13. Synthetic PEG-4MAL hydrogel for controlled release of Wnt7a. (a) Schematic diagram of Wnt7a-releasing PEG-4MAL hydrogel. (b) Passive and proteolytic Wnt7a release profile with one-phase association fit. Extra sum of squares F-test for comparing curve fit. Mean±SEM. n=4 hydrogels/condition. ****p<0.0001.

Figure 14:
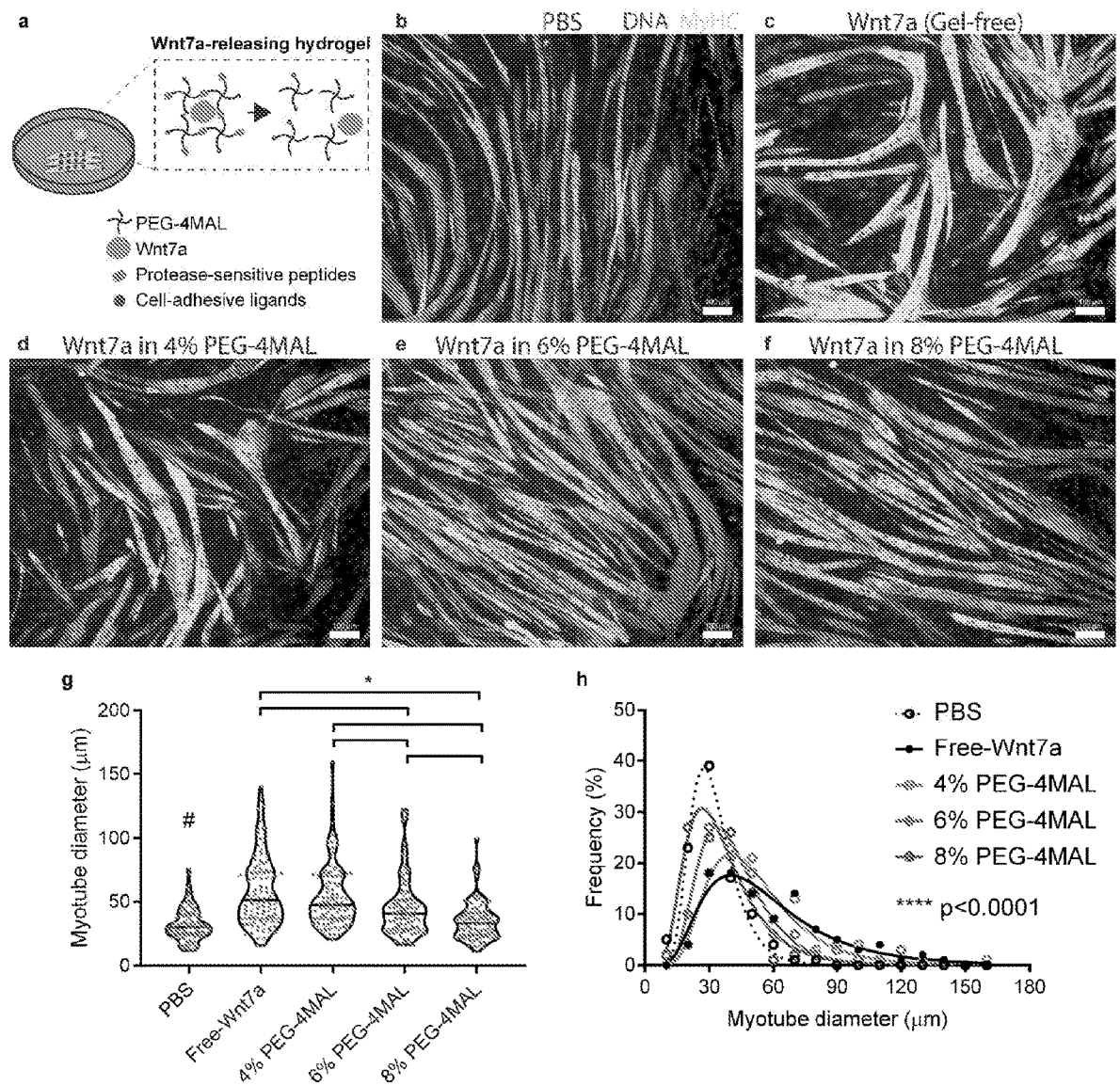

FIG. 14. Hydrogel-released Wnt7a retains its bioactivity in vitro. (a) Schematic diagram of the experiment. Differentiating C2C12 myotubes treated with (b) PBS, (c) Wnt7a (gel-free), (d) Wnt7a in 4% PEG-4MAL hydrogel, (e) Wnt7a in 6% PEG-4MAL hydrogel, and (f) Wnt7a in 8% PEG-4MAL hydrogel. Day 5. Scale bar 100 μm. (g) Violin plot of myotube diameter. n=100 myotubes/condition. Kruskal-Wallis test with Dunn's multiple comparisons test. #p<0.001 vs. free-Wnt7a, 4% PEG-4MAL, and 6% PEG-4MAL. *p<0.05. (h) Histogram of myotube diameter distribution with the log-Gaussian fit. Extra sum of squares F-test for comparing curve fit. ****p<0.0001.

Figure 15:
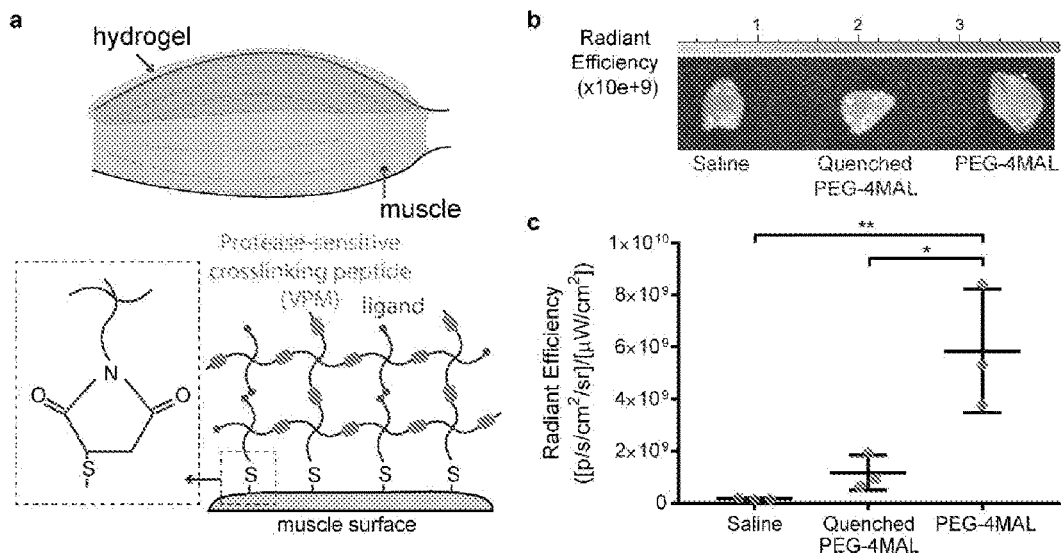

FIG. 15. PEG-4MAL macromer adheres to the muscle surface. (a) Schematic diagram illustrating the ability of PEG-4MAL hydrogel to adhere to the muscle surface via maleimide-thiol reaction. (b) Representative IVIS images of TA muscles treated control (saline), quenched PEG-4MAL macromers conjugated with DyLight™-755-labeled RDG peptides, and PEG-4MAL macromers conjugated with DyLight™-755-labeled RDG peptides. (c) Quantification of radiant efficiency. One-way ANOVA with Tukey's multiple comparisons test. *p<0.05, **p<0.01.

Figure 16:
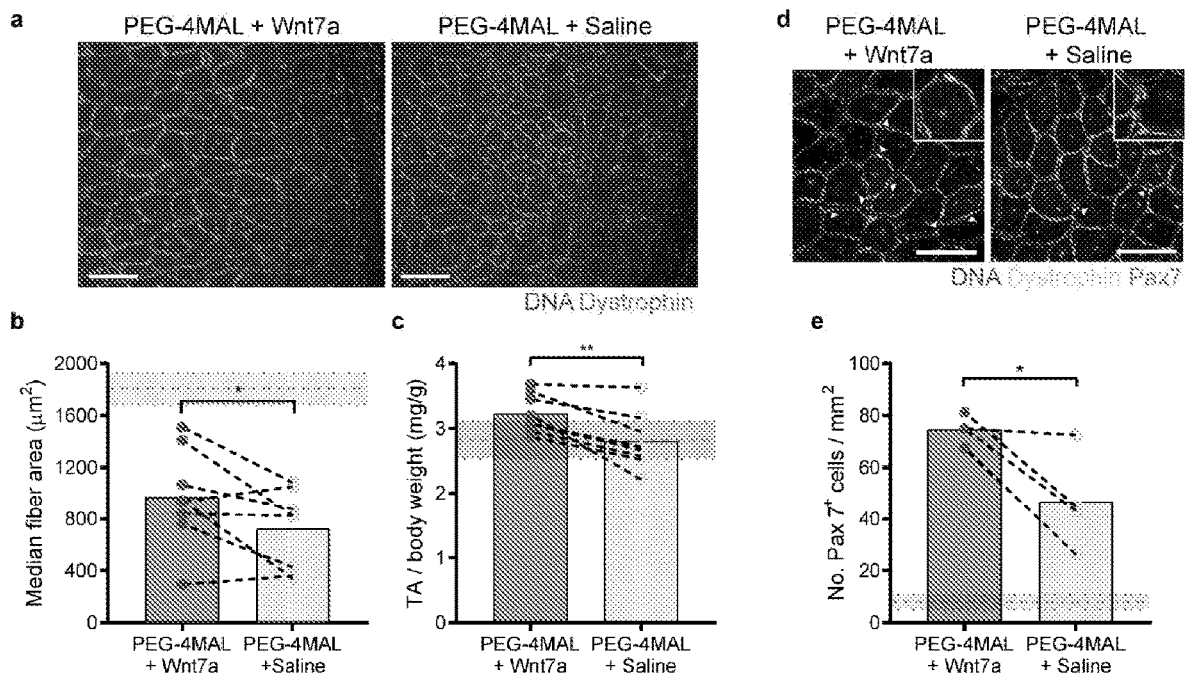

FIG. 16. Engineered PEG-4MAL hydrogel enables effective local delivery of Wnt7a to the injured skeletal muscle. (a) Representative images of TA muscles of C57Bl/6 mice treated with PEG-4MAL hydrogels loaded with Wnt7a or saline. Day 14 post-treatment. Scale bar 100 μm. (b) Median fiber area. Day 14 post-treatment. Two-tailed paired t-test. Grey shaded area and lines indicate median and interquartile range of uninjured reference control (n=4). (c) Mass of TA muscles normalized to the respective body weight. Day 14 post-treatment. Two-tailed paired t-test. Grey shaded area and lines indicate mean±standard deviation of uninjured reference control (n=4). (d) Representative images of TA muscles of C57Bl/6 mice treated with PEG-4MAL hydrogels loaded with Wnt7a or saline. Arrows indicate $Pax7^+$ muscle stem cells. Day 14 post-treatment. Scale bar 100 μm. (e) The number of $Pax7^+$ muscle stem cells per $mm^2$. Day 14 post-treatment. Two-tailed paired t-test. Grey shaded area and lines indicate mean±standard deviation of uninjured reference control (n=4). *p<0.05, **p<0.01.

Figure 17:
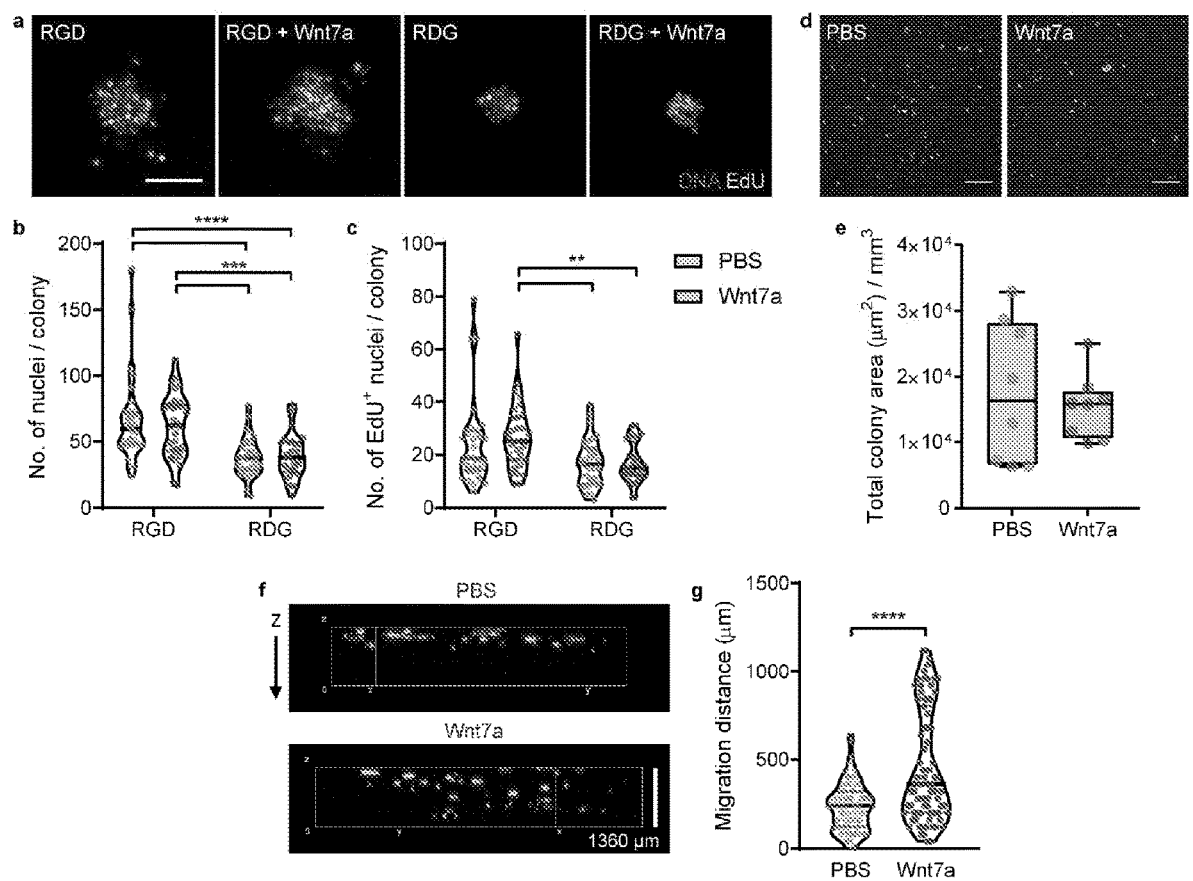

FIG. 17. Wnt7a does not increase MuSC proliferation but promotes muscle stem cells migration through the engineered PEG-4MAL hydrogel. (a) Representative confocal images of myogenic colonies formed in RGD-presenting PEG-4MAL hydrogel, RGD-presenting PEG-4MAL hydrogel with Wnt7a, RDG-presenting PEG-4MAL hydrogel, and RDG-presenting PEG-4MAL hydrogel with Wnt7a. Scale bar 50 μm. (b) Violin plot of myogenic colony size. Two-way ANOVA with Sidak's multiple comparisons test. n=32 colonies/condition. (c) Violin plot of EdU quantification. Two-way ANOVA with Sidak's multiple comparisons test. n=32 colonies/condition. (d) Representative confocal images of nuclei-stained myogenic colonies formed in RGD-presenting PEG-4MAL hydrogels with or without Wnt7a. Scale bar 500 μm. (e) Colony density quantified by total colony area per volume. (f) 3D projection of GFP+ muscle stem cells migrating through the hydrogel from the top surface. (g) Violin plot of cellular migration distance. Day 3. n=79-74 cells/condition. Mann-Whitney test. p<0.01, *p<0.001, ****p<0.0001.

Figure 18:
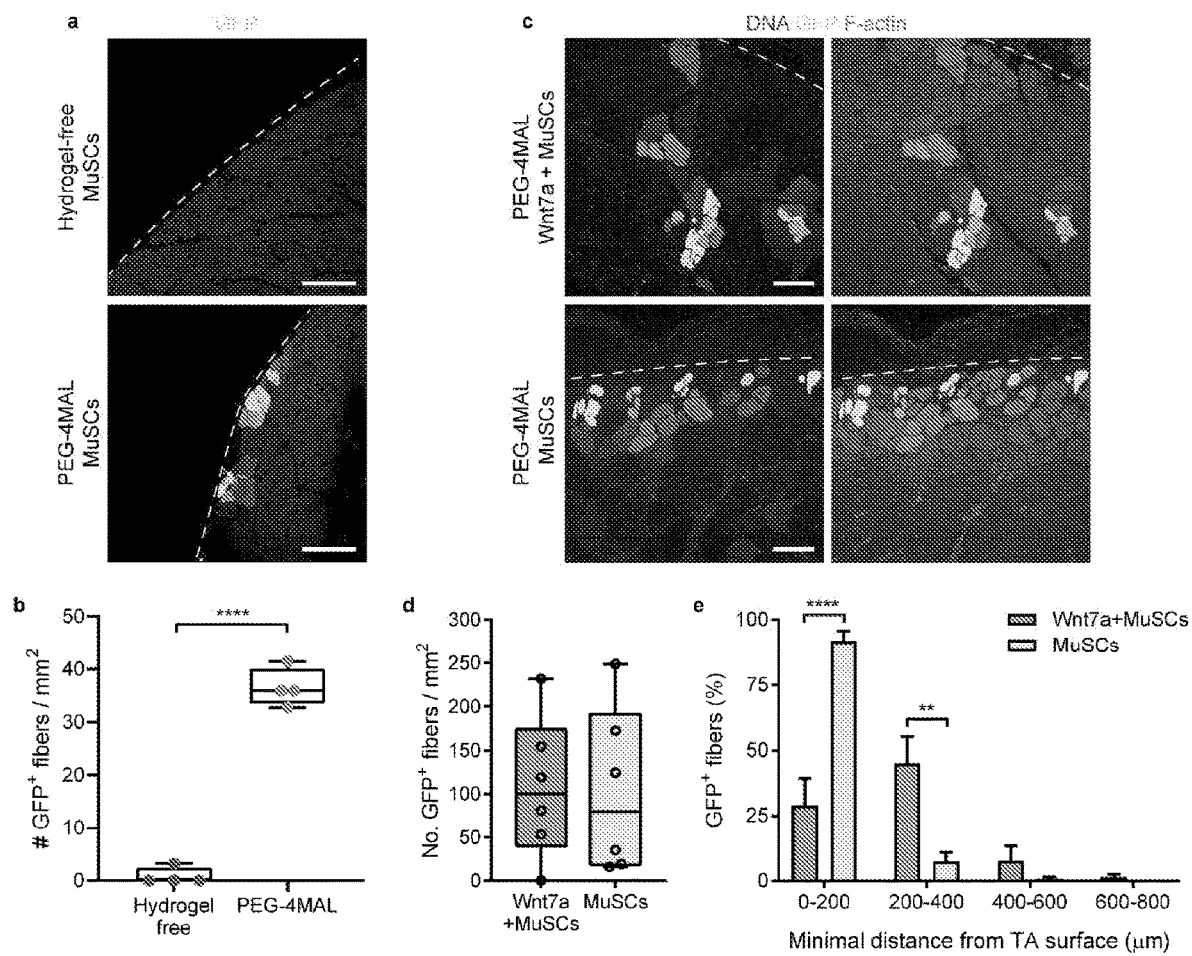

FIG. 18. Wnt7a increases migration potential of PEG-4MAL-released muscle stem cells in vivo. (a) Representative confocal images of TA muscles of immunocompetent mdx mice. Muscle stem cells were supramuscularly delivered with or without the engineered PEG-4MAL hydrogel. 40,000 cells delivered per TA. Day 28 post-treatment. Scale bar 250 μm. Dashed line indicates muscle surface. (b) The number of engrafted $GFP^+$ fibers. Day 28 post-treatment. Two-tailed unpaired t-test. (c) Representative confocal images of TA muscles of immunocompetent mdx mice supramuscularly treated with muscle stem cells encapsulated in PEG-4MAL hydrogels with or without Wnt7a. 50,000 cells delivered per TA. Day 28 post-treatment. Scale bar 100 μm. The dashed line indicates muscle surface. (d) The number of engrafted $GFP^+$ fibers. Day 28 post-treatment. Two-tailed paired t-test. (e) Histogram of $GFP^+$ fibers (%) as a function of minimal distance from the TA surface. Day 28 post-treatment. Two-way repeated measures ANOVA with Sidak's multiple comparisons test. p<0.01, **p<0.0001.

Figure 19:
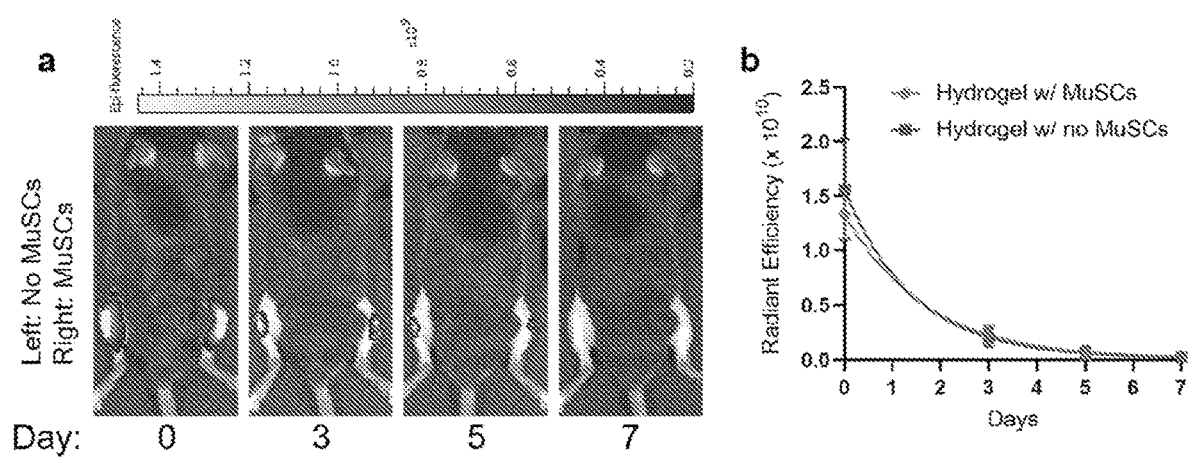

FIG. 19. PEG-4MAL hydrogel fully degrade in vivo within seven days as measured by (A) epi-fluorescence; (B) radiant efficiency.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Disclosed herein are synthetic hydrogels capable of repairing damaged muscle tissue, for instance damaged diaphragm muscle tissue. The compositions contain at least one pro-myogenic agent, for instance muscle satellite cells (MuSC), pro-myogenic proteins, or a combination thereof. Exemplary pro-myogenic proteins include Wnt7a, FGF2, VEGF, IGF-1, BDNF, GDNF, MG53, and combination thereof.

When the composition includes muscle satellite cells, the cells can be present in an amount from $0.2-10 \times 10^3$ cells/μl hydrogel, $0.5-10 \times 10^3$ cells/μl hydrogel, $1-10 \times 10^3$ cells/μl hydrogel, $2.5-10 \times 10^3$ cells/μl hydrogel, $5-10 \times 10^3$ cells/μl hydrogel, 0.2-5×10³ cells/μl hydrogel, 0.2-2.5×10³ cells/μl hydrogel, 0.2-1×10³ cells/μl hydrogel, 1-5×10³ cells/μl hydrogel, or 2.5-7.5×10³ cells/μl hydrogel.

The composition can include one or more pro-myogenic proteins in an amount from 1-1,000 ng/μl hydrogel, from 100-1,000 ng/μl hydrogel, from 500-1,000 ng/μl hydrogel, from 1-100 ng/μl hydrogel, from 50-250 ng/μl hydrogel, from 250-750 ng/μl hydrogel, from 100-200 ng/μl hydrogel, or from 200-400 ng/μl hydrogel.

The synthetic hydrogels include a network of crosslinked hydrophilic polymer conjugated to adhesion peptides. Suitable hydrophilic polymers include polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. The molecular weight of the hydrophilic polymer can be from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer is a polyethylene glycol, i.e., PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In preferred embodiments, the crosslinked hydrophilic polymer is a branched or multi-arm polymer. As used herein, a multi-arm polymer describes a polymer having a central core with at least two polymers covalently attached thereto. Multi-arm polymers can have 2, 3, 4, 5, 6, 7, 8 or more polymer arms. Preferred multi-arm polymers, as defined above, include those with 4 arms. Generally, all of the polymers attached to the core are the same, but in some instances, different hydrophilic polymers, as defined above, can be used. Suitable cores include those derived from polyols, including glycerol (3-arm), pentaerythritol (4-arm), tetraglycerol (6-arm), and hexaglycerol (8-arm). A particularly preferred polymer is a 4-arm PEG, having a total molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer network can have the general formula:

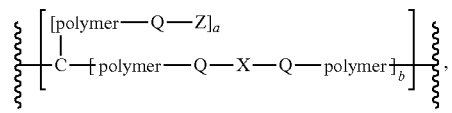

wherein 'polymer' in each case independently represents any hydrophilic polymer, including those defined above, C represents a core, Q represents a linker, Z represents an adhesion peptide, X represents a crosslinker, a is greater than 0, and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

In some embodiments, the hydrophilic polymer can be a poly(ethylene glycol), i.e., networks having the formula:

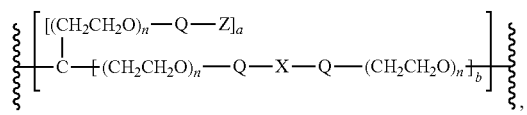

wherein C represents a core, n is an integer from 20-2,000, Q is a linking moiety, Z is an adhesion peptide, X is a crosslinker, a is greater than 0 and b is greater than 1. In some embodiments, the sum a+b is no greater than 3, no greater than 4, no greater than 5, no greater than 6, no greater than 7, no greater than 8, no greater than 9, or no greater than 10. In other embodiments, the sum a+b is at least 3, at least 4, at least 5, no at least 6, at least 7, at least 8, at least 9, or at least 10.

Suitable C groups can be derived from a polyol such as glycerol, pentaerythritol, sorbitol, mannitol, tetraglycerol, and hexaglycerol. In some instances, the core can have the general structure:

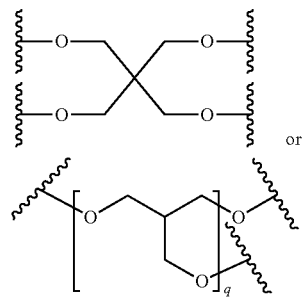

wherein q is any integer, for instance 1, 2, 3, 4, 5, 6, 7, 8, 9, or 10 and ⁀ represents a link to a hydrophilic polymer, as described above. Other suitable polyols include carbohydrates, including monosaccharides and di-saccharides, such as glucose, xylose, mannose, galactose, sucrose, maltose, trehalose and fructose, and cyclic polyols like cyclopropane-1,2,3-triol, cyclobutane-1,2,3,4-tetraol, cyclopentane-1,2,3,4-tetraol, cyclopentane-1,2,3,4,5-pentaol, cyclohexane-1,2,4,5-tetraol, cyclohexane-1,2,3,4,5,6-hexaol, and the like.

Suitable Q group include those formed via Michael addition between a nucleophilic group on the adhesion peptide or crosslinker, and a Michael acceptor bonded to the hydrophilic polymer. For instance, in some embodiments, Q represents a group having the formula:

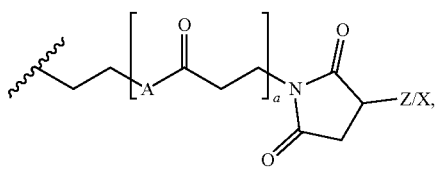

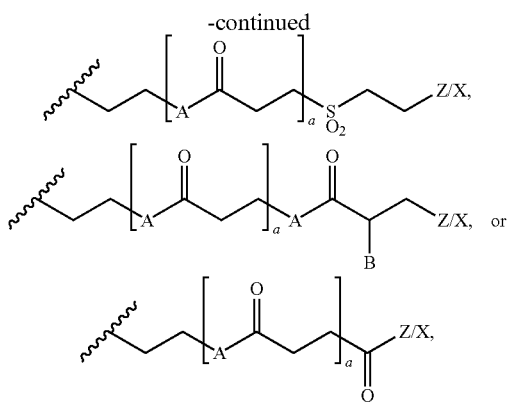

wherein A is independently selected from O or NH, a is independently selected from 0 or 1, B is selected from hydrogen or methyl, Z/X in each case independently represents either an adhesion peptide or crosslinker, and represents a link to a hydrophilic polymer, as described above.

In some embodiments, the adhesion peptide can include the sequence RGD. In some embodiments, the adhesion peptide can include GRGDSPC (SEQ ID NO: 1), CRGDS (SEQ ID NO: 2), CRGDSP (SEQ ID NO: 3), CPHSRN (SEQ ID NO: 4), CGWGGRGDSP (SEQ ID NO: 5), CGGSIDQVEPYSSTAQ (SEQ ID NO: 6), CGGRNI-AEIIKDI (SEQ ID NO: 7), CGGDITYVRLKF (SEQ ID NO: 8), CGGDITVTLNRL (SEQ ID NO: 9), CGGRYVVLPR (SEQ ID NO: 10), CGGKAFDI-TYVRLKF (SEQ ID NO: 11), CGGEGYGEGYIGSR (SEQ ID NO: 12), CGGATLQLQEGRLHFXFDLGKGR, wherein X=Nle (SEQ ID NO: 13), CGGSYWYRIEASRTG (SEQ ID NO: 14), CGGGEFYFDLRLKGDKY (SEQ ID NO: 15), CKGGNGEPRGDTYRAY (SEQ ID NO: 16), CKGGPQVTRGDVFTMP (SEQ ID NO: 17), CGGNR-WHSIYITRFG (SEQ ID NO: 18), CGGASIKVAVSADR (SEQ ID NO: 19), CGGTTVKYIFR (SEQ ID NO: 20), CGGSIKIRGTYS (SEQ ID NO: 21), CGGSINNNR (SEQ ID NO: 22), CGGSDPGYIGSR (SEQ ID NO: 23), CYIGSR (SEQ ID NO: 24), CGGTPGPQGIAGQGVV (SEQ ID NO: 25), CGGTPGPQGIAGQRVV (SEQ ID NO: 26), CGGM-NYYSNS (SEQ ID NO: 27), CGGKKQRFRHRNRKG (SEQ ID NO: 28), CRGDGGGGGGGGGGGGPHSRN (SEQ ID NO: 29), CPHSRNSGSGSGSGSGRGD (SEQ ID NO: 30), Acetylated-GCYGRGDSPG (SEQ ID NO: 31), ((GPP)5GPC) (SEQ ID NO: 32), CRDGS (SEQ ID NO: 33), cyclic RGD{Fd}C (SEQ ID NO: 34), CGGRKRLQVQL-SIRT (SEQ ID NO: 35), CIKVAV (SEQ ID NO: 36), CGGAASIKVAVSADR (SEQ ID NO: 37), CGGKRTGQYKL (SEQ ID NO: 38), CGGTYRSRKY (SEQ ID NO: 39), CGGYGGGP(GPP)5GFOGERPP(GPP)4GPC (SEQ ID NO: 40), CGGKRTGQYKLGSKTGPGQK (SEQ ID NO: 41), QAKHKQRKRLKSSC (SEQ ID NO: 42), SPKHHSQRARKKKNKNC (SEQ ID NO: 43), CGGXBBXBX, wherein B=basic residue and X=hydropathic residue (SEQ ID NO: 44), and CGGXBBBXXBX, wherein B=basic residue and X=hydropathic residue (SEQ ID NO: 45). In some preferred embodiments, the adhesion peptide includes the sequence GRGDSPC. In some instances, the hydrogel can include two or more different adhesions peptides.

In certain embodiments, the following synthetics peptides may be employed:

| Common Name | Sequence | Targets |
|---|---|---|
| RGD | GRGDSPC | $\alpha_v\beta_1$, $\alpha_v\beta_3$, $\alpha_v\beta_5$, $\alpha_v\beta_6$, $\alpha_v\beta_8$, $\alpha_5\beta_1$, $\alpha_8\beta_1$, $\alpha_{IIb}\beta_3$ |
| RDG (scrambled control) | GRDGSPC | N/A (inactive) |
| YIGSR | CGGEGYGEGYIGSR | 67 kDa laminin receptor |
| C16 | CGGKAFDITYVRLKF | Syndecan, $\alpha_v\beta_3$, $\alpha_5\beta_1$, $\beta_1$ |

Suitable crosslinkers include enzymatically cleavable and non-cleavable peptide sequences. The peptide sequences will generally include a cysteine residue at each end of the sequence. Exemplary cleavable peptides include those that are cleavable by MMP, cathepsin, or other proteases. Although the cysteine may be the final amino acid residue at each end of sequence, it is more preferable that the cross-linking peptides are terminated with a glycine or other inert residue. In some embodiments, the enzymatically cleavable peptide will include the dipeptide A-V, N-V, K-V, or Cit-V, in which Cit refers to citrulline. In other embodiments, the crosslinking peptides can include the sequences GCRDGPQG↓IWGQDRCG (SEQ ID NO: 46), GCRDGPQG↓IAGQDRCG (SEQ ID NO: 47), GCRDVPMS↓MRGGDRCG (SEQ ID NO: 48), GCR-DIPVS↓LRSGDRCG (SEQ ID NO: 49), GCRDRPFS↓MIMGDRCG (SEQ ID NO: 50), GCRDVPLS↓LTMGDRCG (SEQ ID NO: 51), GCRDVPLS↓LYSGDRCG (SEQ ID NO: 52), GCR-DIPES↓LRAGDRCG (SEQ ID NO: 53), GCRDSGES-PAY↓YTADRCG (SEQ ID NO: 54), GCRDGGYAE↓L-RMGGDRCG (SEQ ID NO: 55), GCRDGGPLG↓LYAGGDRCG (SEQ ID NO: 56), GCRDGPLG↓LWARDRCG (SEQ ID NO: 57), wherein ↓ represents a cleavable amide bond. In some embodiments, the crosslinker is a not a peptide, for instance a dimercapto compound such as a 1,4-dithiothreitol (1,4-dimercapto-2,3-butanediol) or poly(ethylene glycol) dithiol. In some cases, the hydrogel can include two or more cleavable crosslinkers.

The compositions can include water in an amount of at least 70% by weight relative to the total weight of the composition. In some embodiments, the water can be present in an amount of at least 75%, at least 80%, at least 85%, at least 87.5%, at least 90%, at least 92.5%, or at least 95% by weight relative to the total weight of the composition. In some embodiments, the compositions will include the hydrophilic crosslinked polymer network in an amount no greater than 30%, no greater than 25%, no greater than 20%, no greater than 15%, no greater than 12.5%, no greater than 10%, no greater than 7.5%, or no greater than 5%, by weight relative to the total volume of the hydrogel. In certain embodiments, the crosslinked hydrophilic polymer network is present in an amount from 1-8%, from 2-7%, from 2-6%, from 3-6%, from 3-5%, or from 3.5-4.5% polymer weight by total volume of the composition. In certain embodiments, the crosslinked hydrophilic polymer network is present in an amount of about 3% or about 4% polymer weight by total volume of the composition.

The crosslinked networks disclosed herein may be prepared by first conjugating an adhesion peptide to a hydrophilic polymer having the formula:

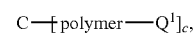

$$C-[\text{polymer}-Q^1]_c,$$

wherein C and "polymer" are as defined above, c is an integer greater than or equal to 3, and $Q^1$ is an electrophilic group capable of reacting with a thiol group. In some embodiments, the hydrophilic polymer is PEG, i.e., a compound of formula:

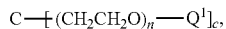

wherein C, n, c, and $Q^1$ are as defined above. In some embodiments, $Q^1$ represents a group having the formula:

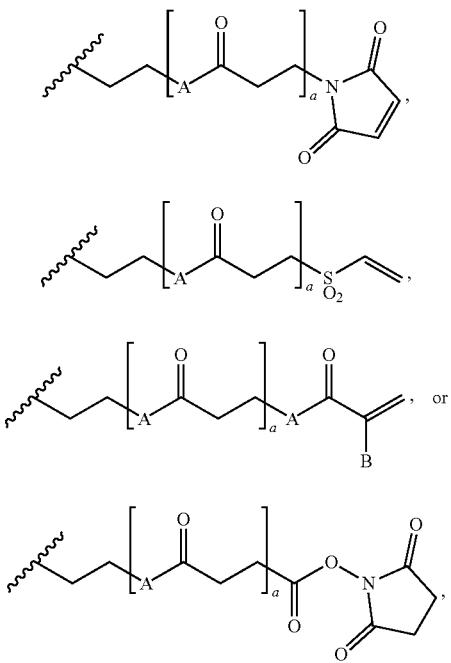

wherein A is independently selected from O or NH, a is independently selected from 0 or 1, B is selected from hydrogen or methyl, and represents a link to a hydrophilic polymer, as described above.

The adhesion peptide can contain a single cysteine residue or thiol group and will be combined such that there is a molar excess of $Q^1$ groups relative to cysteine/thiol groups in the adhesion peptide. For instance, molar ratio of $Q^1$ groups to cysteine/thiol residues can be from 10:1 to 1.5:1, from 8:1 to 1.5:1, from 6:1 to 1.5:1, from 4:1 to 1.5:1, from 3:1 to 1.5:1, from 2.5:1 to 1.5:1, from 5:1 to 2:1, from 5:1 to 3:1, or from 5:1 to 4:1. The molar ratio of nucleophilic groups in the crosslinker to unreacted $Q^1$ groups (assuming complete reaction with adhesion peptide) can be 1:1, greater than 1:1, e.g., 1.1:1, 1.2:1, or 1.5:1, less than 1:1, e.g., 0.9:1, 0.8:1, or 0.5:1, from 0.5:1 to 1.5:1, from 0.75:1 to 1.25:1, from 0.5:1 to less than 1:1, or from 1.5:1 to greater than 1:1.

Each of the hydrophilic polymer, adhesion peptide, crosslinker, and myogenic agent(s) can be separately combined with an appropriate aqueous solution, generally buffered to a pH from 5.0-8.0, from 5.0-7.0, from 5.0-6.5, from 5.0-6.0, from 5.5-6.0, from 5.5-6.5, from 6.5-7.5, from 7.2-7.6, or from 7.3-7.5. A physiologically compatible buffer may be used, such as 4-(2-hydroxyethyl)piperazine-1-ethanesulfonic acid (HEPES), phosphate buffers, carbonate buffers, tromethamine (tris) buffers, including those formed with EDTA and an acid such as acetic acid, boric acid, and the like.

The relative ratios of the components may be as follows:

| Hydrogel component | Volume fraction of hydrogel component | Concentration factor of hydrogel component |
|---|---|---|
| Hydrophilic polymer | 0.3-0.5 | 2.5× |
| Adhesion peptide | 0.15-0.25 | 5× |
| Crosslinker | 0.15-0.25 | 5× |

The hydrophilic polymer may be combined with a solution of adhesive peptide such that the final adhesive peptide concentration is from 0.1-100 mM, from 0.5-75 mM, from 1-50 mM, from 5-25 mM, or from 7.5-15 mM, based on the total volume of the hydrogel. The mixture can be incubated at a temperature from 23-50° C., from 28-45° C., from 32-40° C., or at 37° C. for at least 5 minutes, at least 10 minutes, at least 15 minutes, or at least 20 minutes. The resulting product is designated the hydrogel precursor, which has the following structure:

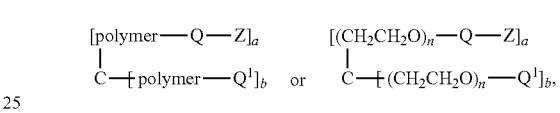

wherein C, 'polymer,' n, Q, $Q^1$, Z, a, and b have the meanings given above. The hydrogel precursor may be directly converted to a hydrogel by combination with the crosslinker or may first be combined with the myogenic agent(s) and subsequently combined with the crosslinker to form the hydrogel.

The compositions disclosed herein may be used to promote healing and repair of muscle tissue, especially for diaphragm muscle tissue. In certain embodiments, the compositions disclosed herein can be used to treat diaphragm muscle damaged as a result of trauma, while in other embodiments the compositions can be used to treat diaphragm muscle damaged as a result of disease. For instance, the compositions may be advantageously employed to treat patients with muscular dystrophy, such as Duchenne-type muscular dystrophy, Becker muscular dystrophy, myotonic muscular dystrophy, facioscapulohumeral muscular dystrophy, congenital muscular dystrophy, or limb-girdle muscular dystrophy. The compositions may be used to treat diaphragm injury or damage in adult and/or pediatric patients, for instance those less than 18 years of age, less than 12 years of age, less than 8 years of age, less than 4 years of age, or less than 1 year of age. In yet other embodiments, the compositions may be used to treat geriatric patients, for instance those patients greater than 65 years of age. In other embodiments, the compositions may be used to treat muscle injury in non-human animals.

In some instances, a preformed hydrogel composition may be directly contacted with the damaged muscle tissue. In other instances, the composition may be administered subcutaneously adjacent or proximate to the tissue. In some embodiment a hydrogel precursor is combined with a crosslinker at the tissue at the time of administration. In such embodiments, the myogenic agent may be first combined with either of the hydrogel precursor or crosslinker. A preferred method includes an in vivo hydrogel formation. The hydrogel precursor is loaded into a dispensing means, for instance a syringe, which is in fluid communication with a needle by way of a tube. Inside the tube is loaded the crosslinker, such that when the hydrogel precursor is expelled from the syringe, it combines with the crosslinker solution and is ejected from the needle into the directed site. The myogenic agents, i.e., MuSC and/or pro-myogenic protein, may be combined with either the hydrogel precursor, crosslinker, or both.

In certain embodiments, micropunctures may be formed on the damaged tissue to enhance muscle repair. The micropunctures may be formed by contacting the muscle tissue with a substrate comprising at least one microneedle. The substrate can be a flat panel or a cylinder (for instance a roller). In certain embodiments, the substrate can be included with a plurality of microneedles in a variety of configurations such as a grid or concentric circles. The microneedles can be spaced apart from the other microneedle by a distance from 0.1-10 mm, from 0.1-5 mm, from 0.1-2.5 mm, from 0.1-1 mm, from 0.5-2.5 mm, from 0.5-1.5 mm, or 1 mm.

Suitable microneedles can an average effective length from 50-5,000 µm, from 50-2,500 µm, from 50-1,000 µm, from 50-500 µm, from 50-250 µm, from 50-100 µm, from 1,000-5,000 µm, or from 500-1,000 µm; and an average diameter from 10-500 µm, from 50-500 µm, from 100-500 µm, from 250-500 µm, from 10-100 µm, from 25-250 µm, from 50-150 µm, or from 100-250.

The micropunctures can be formed on the muscle tissue prior to application of the hydrogel (or hydrogel precursor) composition to the tissue. In some embodiments, the hydrogel (or hydrogel precursor) composition can be painted on a surface of the substrate bearing microneedles, such that the micropunctures are formed more or less simultaneously with the application of the composition. In yet further embodiments, the hydrogel composition can first be applied to the muscle tissue, followed by formation of micropunctures.

Also provided herein are kits that include the disclosed hydrogel or hydrogel precursor composition and a substrate having at least one microneedle, such as described above.

EXAMPLES

The following examples are for the purpose of illustration of the invention only and are not intended to limit the scope of the present invention in any manner whatsoever.

Example 1: Preparation and Evaluation of MuSC Loaded Hydrogels

Animals: C57Bl/6, B6Ros.Cg-DMD$^{mdx-4CV}$/J, FVB-Tg(CAG-luc,-GFP)L2G85Chco/J, B6.Cg-Gt(ROSA)$^{26ortm14(CAG-TdTomato)Hze}$/J and B6.C-Tg(CMV-cre)lCgn/J mice were obtained from Jackson Laboratory. C57Bl/6-βactin-EGFP mice were provided by Dr. Amy Wagers, Harvard University. R26R-TdTomato/CMV-cre mice were acquired by crossing B6.Cg-Gt(ROSA)$^{26Sortm14(CAG-TdTomato)Hze}$/J and B6.C-Tg(CMV-cre)lCgn/J mice. CAG-luc-Ka-βactin-EGFP mice were acquired by crossing FVB-Tg(CAG-luc,-GFP) L2G85Chco/J and C57Bl/6-βactin-EGFP mice. Both male and female mice were used in this study in a randomized manner. Mice were housed, aged and/or bred in the Physiological Research Laboratory Animal Facility of Georgia Tech. All animal procedures were conducted under the approval of the Institutional Animal Care and Use Committee (IACUC) of Georgia Tech.

MuSC isolation: Hindlimb muscles were dissected from 2-4 months old mice, minced, and digested in DMEM containing type II collagenase (0.2%; Worthington Biochemical Corp) and dispase II (2.5U·ml$^{-1}$; Roche) for 90 min. at 37° C. The digest solution containing the muscles was triturated every 30 min. using a donor bovine serum (DBS)-coated serological pipette. A two-part volume of 20% DBS in F10 media was added to the digested solution and filtered through a 70-µm cell strainer. The solution was centrifuged (300 g) for 5 min. at 4° C. to yield cell pellets. Cell pellets were washed using 2% DBS in HBSS (300 g centrifugation for 5 min. at 4° C.) and re-suspended in 2% DBS in HBSS. Cells were incubated with a cocktail of primary antibodies (1:100) consisting of PE-conjugated anti-mouse β1 integrin (CD29, 20.0%, Biolegend), APC-conjugated anti-mouse Sca1 (13.3% v/v, Biolegend), CD45 (13.3%, Biolegend), CD11b (13.3%, Biolegend), Ter119 (13.3%, Biolegend), biotinylated anti-mouse CD184 (CD184, 26.8%, BD Pharmigen) in 2% DBS in HBSS for 30 min. on ice. Cells were washed in in 2% DBS in HBSS, and subsequently incubated with secondary antibody (Streptavidin-PE-Cy7; 1:100; eBioscience) for 20 min. on ice. Stained cells were washed as above, and propidium iodide$^-$, Sca1$^-$, CD45$^-$, CD11b$^-$, Ter119$^-$, β1 integrin$^-$, CXCR4$^+$ cells were sorted via fluorescence-activated cell sorting using BD FACS Aria IIIu Cell Sorter.

Hydrogel synthesis, cell encapsulation, and culture: Four-arm PEG-4MAL macromer (MW 22,000 or 10,000; Laysan Bio) was dissolved in 1×PBS containing 10 mM HEPES (pH 7.4). Cell adhesive peptides (GRGDSPC, GRDGSPC, CGGEGYGEGYIGSR, CGGKAFDITYVRLKF; >95% purity; Genscript) were dissolved in 1×PBS containing 10 mM HEPES and added to PEG-4MAL solution to produce functionalized PEG-4MAL precursors. Freshly isolated MuSCs were then added to the solution containing functionalized PEG-4MAL precursors. To synthesize cell-encapsulated hydrogels, the solution containing functionalized PEG-4MAL precursors and cells was mixed with protease-degradable crosslinking peptide (GCRDVPMSRGGDRCG; Genscript) or non-degradable hexa(ethylene glycol) dithiol (Sigma-Aldrich) dissolved in 1×PBS containing 10 mM HEPES, and subsequently polymerized at 37° C./5% $CO_2$ for 5 min. prior to adding MuSC growth media (F10 containing 1% penicillin/streptomycin, 1% Glutamax, and 20% horse serum). Recombinant human FGF-2 (25 ng·ml$^{-1}$, Peprotech) was supplemented daily. To prime the MuSCs to differentiate, the growth medium was replaced with differentiation media (DMEM containing 1% penicillin/streptomycin, 1% Glutamax, and 2% horse serum) on day 5-6 of culture. Cells were cultured in the differentiation media for additional 4 days.

Cell encapsulation in collagen gel: Freshly isolated MuSCs (10,000 cells/gel) were added to the rat-tail collagen type I working solution consisting of 200 mM HEPES (10.4% v/v), 10× DMEM (10.4%), 7.5% $NaHCO_3$ (5.2%), and 5 mg·ml$^{-1}$ collagen I (54%; Rat Collagen I, Culturex®, Lot #30871G14). Prior to adding cells, pH of the collagen working solution was adjusted by adding 1M NaOH. pH-adjusted, cell-containing collagen solution was polymerized at 37° C./5% $CO_2$ for 30 min. prior to adding MuSC growth media. Recombinant human FGF-2 (25 ng·ml$^{-1}$) was supplemented daily.

Cell encapsulation in Matrigel: Freshly isolated MuSCs (10,000 cells; 2/10 part) were added to the Matrigel (8/10 part; Phenol and LDEV-free, Corning, Lot #5075010). Cell-containing Matrigel was polymerized at 37° C./5% C02 for 45 min. prior to adding MuSC growth media. Recombinant human FGF-2 (25 ng·ml$^{-1}$) was supplemented daily.

In vitro cell staining and myogenic colony quantification: For EdU (5-ethynyl-2' deoxyuridine) labeling, cells encapsulated in hydrogels were incubated in growth media containing 10 µM EdU for 6 hours. Hydrogels were fixed in 4% paraformaldehyde for 20 min. and subsequently washed in 1×PBS three times. Cells within the hydrogels were blocked and permeabilized using blocking buffer (5% BSA, 0.5% goat serum, 0.5% Triton-X in 1×PBS) for 1 hour at room temperature. EdU detection was performed per the manufacturer's instructions (Invitrogen). TUNEL (terminal deoxynuceotidyl transferase-dUTP nick end labeling) staining and detection were performed per the manufacturer's instructions (Invitrogen). Hydrogels were incubated with primary antibodies overnight at 4° C., washed in 1×PBS three times, incubated with secondary antibodies containing Hoechst (1:1000) overnight at 4° C., and washed in 1×PBS three times. Z-stack projection images were acquired using a confocal microscope (Nikon Eclipse Ti-E C2+). Myogenic colony morphology, size, and percent EdU$^+$ nuclei were automatically quantified using ImageJ and CellProfiler. Cell packing density was measured by segmenting the colony of interest, converting DAPI channel of a MuSC colony into a binary image (white pixel value=255 and black pixel value=0), and subsequently determining the mean pixel value, where the resulting value ranges from 0 (less dense) to 255 (more dense). The mean pixel values were then normalized by dividing by 255 to obtain a "cell packing density" metric that ranges from 0 (less dense) to 1 (more dense). The fusion index was determined by taking the percentage of nuclei contained in multinucleated myotubes with at least 2 nuclei.

TOTO-3 iodide dead cell labeling: Freshly isolated β-actin-GFP$^+$ MuSCs were encapsulated in either PEG-4MAL or collagen gels and cultured in growth media overnight. TOTO-3 iodide (Invitrogen) was then added to the media at final concentration of 1 μM. Cells were incubated at 37° C./5% $CO_2$ for 30 min. Z-stack projection images were acquired using a confocal microscope (Nikon Eclipse Ti-E C2$^+$) equipped with LiveCell™ system (Pathology Devices Live Cell) at 37° C./5% $CO_2$/50% RH. TOTO-3$^+$ dead cells were quantified by taking the percentage of TOTO-3$^+$ nuclei over total cell number.

Taqman RT-PCR: Primary MuSCs were cultured in RGD or RDG-presenting hydrogels in the growth media for 6 days and differentiated in the differentiation media for additional 5 days. Hydrogels were mechanically homogenized, and RNA was extracted using TRIzol Reagent (Thermo Fisher). Quality and amount of RNA was assessed using NanoDrop (Thermo Fisher) at $A_{260/280}$. cDNA was obtained using High-Capacity cDNA Reverse Transcription Kit per manufacturer's instructions (Thermo Fisher). RT-PCR was performed using TaqMan assay primers (Myogenin, Desmin, Gapdh, βactin probes) and Taqman Fast Advanced Master Mix per manufacturer's instructions (Thermo Fisher). Ct values of Myogenin and Desmin were normalized to the geometric mean of Gapdh and βactin control genes. Fold differences were determined using $2^{-ddCt}$.

Rheological testing and mesh size estimation: Hydrogels were casted in Sigma cote-treated (Sigma-Aldrich) cylindrical molds consisting of a glass slide and a silicone isolator. Upon gelation at 37° C., hydrogels were extracted and swelled in 1×PBS at 4° C. overnight. Cell-containing hydrogels were synthesized and cultured in growth media as described above for 12 hours, 2, 3, and 5 days. Fully swollen hydrogels were tested using a rheometer (Anton Paar MCR-302; CP10-2) at 37° C. Frequency sweep (100-0.1 rad/s) was performed at a constant strain of 1%. G' and G" were determined by averaging all data points acquired from 10-0.1 rad/s interval. Mesh size was estimated using the following equation:

$$\xi = \left(\frac{G'A}{RT}\right)^{-\frac{1}{3}}$$

where G'=storage modulus in Pa, A=Avogadro's constant, R=gas constant, T=temperature.

One-dimensional diffusion assay: Hydrogel was casted at one end of a glass capillary tube (1 mm O.D. and 0.58 mm I.D.; World Precision Instruments) using an insulin syringe. Hydrogel-containing capillary tubes were placed in a 50 ml conical tube containing 1× PBS to fully swell overnight at 4° C. Alexa-555-labeled α-bungaroxin (8 kDa; 1:4 dilution in PBS; Thermo Fisher) was delivered to the other free end of the hydrogel-containing glass capillary tube. Samples were immediately placed in the temperature and humidity-controlled stage of an epi-fluorescence microscope (Zeiss Observer D1). Time-series images were acquired every 15 min. for 3 hours at 37° C. Hydrogel boundary (x=0) was defined by a region with average raw intensity of 9.5 at t=0. Change in the average intensity was quantified from x=0 to 200 μm over the 3-hour assay period. To determine the diffusion coefficient (D), the data was fitted using the solution of Fick's second law:

$$\varphi(x, t) = \varphi_0 \cdot \text{erfc}\left(\frac{x}{2\sqrt{Dt}}\right)$$

Cryo-injury, MuSC transplantation, and injections: Mice were anesthetized by inhalation of isoflurane. The hair over TA and gastrocnemius muscles was depilated to expose the skin. A small incision was made through the skin and fascia to expose the TA. A liquid nitrogen-cooled metal probe was placed on the surface of the exposed TA for 10 sec. to induce cryo-injury. Immediately upon muscle recovery, freshly isolated MuSCs were delivered on the locus of the injured TA either in suspension (2% DBS in HBSS), in 2.7 mg·ml$^{-1}$ rat-tail collagen type I (Culturex® Lot #30871G14), or in the bioengineered hydrogels. For the hydrogel-mediated delivery, the cell encapsulated hydrogel was casted directly on the surfaced of the injured TA. The skin incision was carefully sutured (Vicryl suture, Ethicon). All rodent survival procedures were performed using aseptic procedures.

Longitudinal bioluminescence imaging: Longitudinal bioluminescence imaging was performed using the IVIS SpectrumCT In Vivo Imaging System (Perkin Elmer). Prior to imaging, mice were anesthetized by inhalation of isoflurane, and hindlimbs were depilated. 300 μl luciferin-D (4 mg; Promega) was injected intraperitoneally, and mice were imaged every 5 min. up to 120 min. to determine the maximal signal. The maximum signal was determined for each TA and used for the subsequent analyses.

Tissue histology and immunostaining: Hind limbs were harvested and fixed in 4% paraformaldehyde for 1 hour at room temperature, and subsequently incubated in 30% sucrose overnight at 4° C. TA muscles were dissected and frozen in liquid nitrogen-cooled isopentane. Frozen muscles were sectioned to 10 μm thickness. Prior to antibody staining, tissue sections were blocked and permeabilized using blocking buffer (5% BSA, 0.5% goat serum, 0.5% Triton-X in 1×PBS) for 1 hour at room temperature. Tissues for hematoxylin and eosin staining were prepared in a similar manner without the sucrose pre-treatment.

GFP fiber quantification: For quantifying number of GFP$^+$ fibers in tissue sections, GFP channel images of anti-GFP antibody-stained tissue sections were acquired using an epi-fluorescence microscope (Zeiss Observer D1) or a confocal microscope (Zeiss LSM 700). Images were then converted to 8-bit, and automatic triangle-algorithm thresholds were applied using ImageJ. Based on the processed binary images, GFP$^+$ fibers were objectively identified and scored.

Antibodies and staining reagents: The following primary and secondary antibodies were used to stain cells and tissue sections for immunofluorescence in this study: Pax7 (1:50, DHSB), MyoD (1:200, C-20, Santa Cruz), Myosin heavy chain (1:200, M4276, Sigma-Aldrich), Desmin (1:200, H-76, Santa Cruz), Alexa Fluor 488-conjugated anti-GFP (1:250, A-21311, Thermo Fisher), Alexa Fluor 488 goat anti-mouse IgG (1:250, A-11029, Thermo Fisher), Alexa Fluor 488 goat anti-rabbit IgG (1:250, A-11034, Thermo Fisher), Alexa Fluor 555 goat anti-mouse IgG (1:250, A-21422, Thermo Fisher), and Alexa Fluor 555 goat anti-rabbit IgG (1:250, A-21424, Thermo Fisher). Alexa Fluor 555 phalloidin (1:50, Thermo Fisher) and Alexa Fluor 647 phalloidin (1:50, Thermo Fisher) were used to stain F-actin. Hoechst 33342 (1:1000, Thermo Fisher) and DRAQ-5 (1:1000, Thermo Fisher) were used to counterstain cell nuclei.

Statistical analyses: Sample sizes were chosen based on preliminary experiments to ensure adequate statistical power. Statistical analyses were performed using GraphPad Prism 7. Normality of data was tested using Shapiro-Wilk test, and confirmed graphically via quantile-quantile (QQ) plot. Outliers were detected using Grubb's test. Two-group comparisons were conducted using unpaired two-tailed t-test or Mann-Whitney U test based on the data normality. For paired data, analyses were conducted using paired two-tailed Wilcoxon or t-test based on data normality. For multiple group comparisons, one-way ANOVA with Tukey's post-hoc tests or Kruskal-Wallis test with Dunn's post-hoc tests were performed based on data normality. Two-way ANOVA with Sidak's post-hoc tests were performed for EdU$^+$ nuclei (%) data. Two-way repeated-measures ANOVA was performed on the longitudinal bioluminescence data to compare effects of biomaterial, time, and their interactions. The area under the curve was calculated in GraphPad Prism 7.

Results

Figure 1:
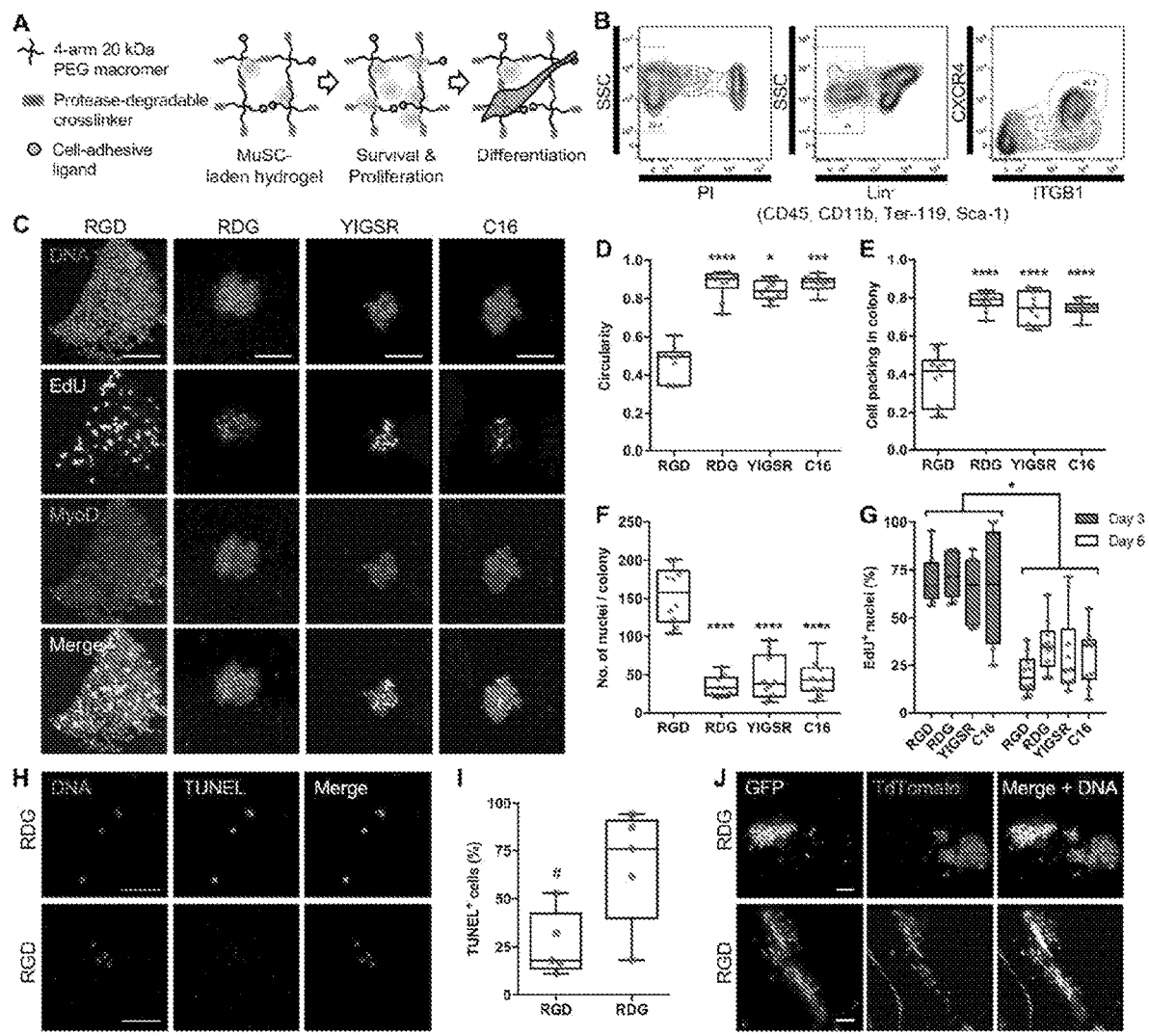
FIG. 1. RGD-presenting PEG-4MAL hydrogels promote MuSC survival, proliferation, and differentiation. (A) Schematic of cell-laden hydrogel. Synthetic hydrogel platform can be biofunctionalized with cell-adhesive ligands and protease-degradable crosslinkers. (B) Representative fluorescence-activated cell sorting plot of MuSCs. (C) Representative z-projections myogenic colonies formed in PEG-4MAL hydrogels presenting synthetic cell adhesive peptides. Day 6. Scale bar: 100 µm. (D) Quantification of myogenic colony circularity. n=9-10 colonies. * p<0.05, * p<0.001,  p<0.0001 vs. RGD via Kruskal-Wallis with Dunn's test. (E) Quantification of myogenic colony cell packing density. n=9-10 colonies.  p<0.0001 vs. all groups via 1-way ANOVA with Tukey's test. (F) Quantification of myogenic colony size. n=9-10 colonies. ** p<0.0001 vs. all groups via 1-way ANOVA with Tukey's test. (G) Quantification of myogenic colony proliferation. n=9-10 colonies. * p<0.05 via 2-way ANOVA with Sidak's test. (H) Representative z-projections of DNA and TUNEL staining. Day 1. Scale bar: 50 µm. (I) Quantification of TUNEL$^+$ cells. n=5 hydrogels. #p<0.05 via unpaired two-tailed t-test. (J) Representative z-projections of GFP$^+$ and TdTomato$^+$ MuSCs. Cells were cultured in growth media for 6 days, then in differentiation media for 4 days. GFP/TdTomato fused cells appear yellow. Scale bar: 100 µm.

We isolated Pax7$^+$ primary MuSCs by flow cytometry using a previously established set of markers (CD45$^-$, CD11b$^-$, Ter119$^-$, Sca1$^-$, CXCR4$^+$, β1-integrin$^+$; FIG. 1B) and encapsulated the cells as non-aggregated single cells in 4% (w/v) PEG-4MAL hydrogels (20 kDa macromer) containing either 1.0 mM RGD, RDG (scrambled control), YIGSR, or C16 synthetic peptides and crosslinked with protease-degradable peptides (FIG. 7). All these hydrogel formulations exhibit equivalent mechanical, diffusive transport, and protease-degradable properties. After 6 days of culture in growth media containing basic fibroblast growth factor (FGF-2), MuSCs cultured in RGD-presenting hydrogels proliferated and formed non-circular MyoD$^+$ myogenic colonies compared to RDG (p<0.0001), YIGSR (p<0.05), and C16-presenting (p<0.001) hydrogels (FIGS. 1C and D). For RGD-presenting hydrogels, cell packing density within a myogenic colony was significantly lower compared to the other hydrogel formulations (p<0.0001), suggesting cellular migration (FIGS. 1C and E). Furthermore, myogenic colonies formed in RGD-presenting hydrogels were significantly larger compared to colonies formed in RDG, YIGSR, and C16-presenting hydrogels (p<0.0001; FIGS. 1C and F). However, when cell proliferation was assessed via EdU (5-ethynyl-2'-deoxyuridine) incorporation, no statistical differences were observed among hydrogels containing different cell-adhesive peptides on both days 3 and 6 of culture (FIGS. 1C and G, FIG. 8A). Furthermore, MuSCs in RGD, RDG, C16, and YIGSR-presenting hydrogels exhibited similar levels of MuSC activation (>60% Pax7$^+$ and >95% MyoD$^+$ activated MuSCs per colony; FIGS. 8B and C) after 72 hours of culture, indicating that potential differences in activation state did not contribute to the differential myogenic colony formation. Notably, MuSCs cultured in RGD-presenting hydrogels exhibited significantly less TUNEL$^+$ cells compared to MuSCs in scrambled RDG-presenting hydrogels at day 1 post-encapsulation (p<0.05), indicating that hydrogels presenting the RGD cell-adhesive peptide promote cell survival and subsequently support the formation of robust myogenic colonies compared to hydrogels presenting scrambled RDG control peptide (FIGS. 1H and I).

To determine if RGD-presenting hydrogels support MuSC differentiation, GFP$^+$ and TdTomato$^+$ MuSCs were mixed in a 1:1 ratio and encapsulated within RGD- or RDG-presenting hydrogels. We reasoned that fused GFP$^+$ and TdTomato$^+$ cells would exhibit both fluorescent proteins in the cytosol, indicative of differentiation and fusion (FIG. S3A). To prime differentiation, MuSCs in either RGD- or RDG-presenting hydrogels were initially cultured in growth media with daily supplementation of FGF-2 for 6 days, then in differentiation media for an additional 4 days. Cells cultured in RDG-presenting hydrogels did not fuse and cells remained in multi-cellular clusters homogeneously composed of either GFP$^+$ or TdTomato$^+$ myoblasts (FIG. 1J and FIG. 9B). In contrast, cells cultured in RGD-presenting hydrogels were morphologically distinct, where the cells were elongated and spread (FIG. 1J and FIG. 9B). Moreover, cell fusion events were present, indicated by multinucleated myotubes expressing both GFP$^+$ and TdTomato$^+$ in the cytosol with significantly higher fusion index compared to control RDG-presenting hydrogels (p<0.0001; FIG. 1J and FIGS. 9B and C). Differentiated myotubes exhibited spontaneous contraction in the RGD-presenting hydrogels, indicating functional differentiation of MuSC. Despite the marked differences in cellular fusion and morphology, cells in both RGD- and RDG-presenting hydrogels stained positive for desmin and myosin heavy chain (MHC) upon culturing in differentiation media (FIG. 9D) and exhibited similar levels of myogenin and desmin gene expression (FIG. 9E). This result suggests that the reduced serum content of the differentiation media primes the cells to differentiate, but cells are unable to undergo fusion in the non-adhesive RDG-presenting hydrogels, corroborating the importance of cell-adhesive ligands in the cellular fusion process. Indeed, β3-integrin, a major target of RGD tripeptide sequence, has been shown to be an essential factor for myotube formation. Collectively, these results indicate that presentation of RGD adhesive peptide in PEG-4MAL hydrogels promotes MuSC in vitro survival, proliferation, and differentiation.

PEG-4MAL Macromer Density Modulates MuSC Proliferation

Figure 2:
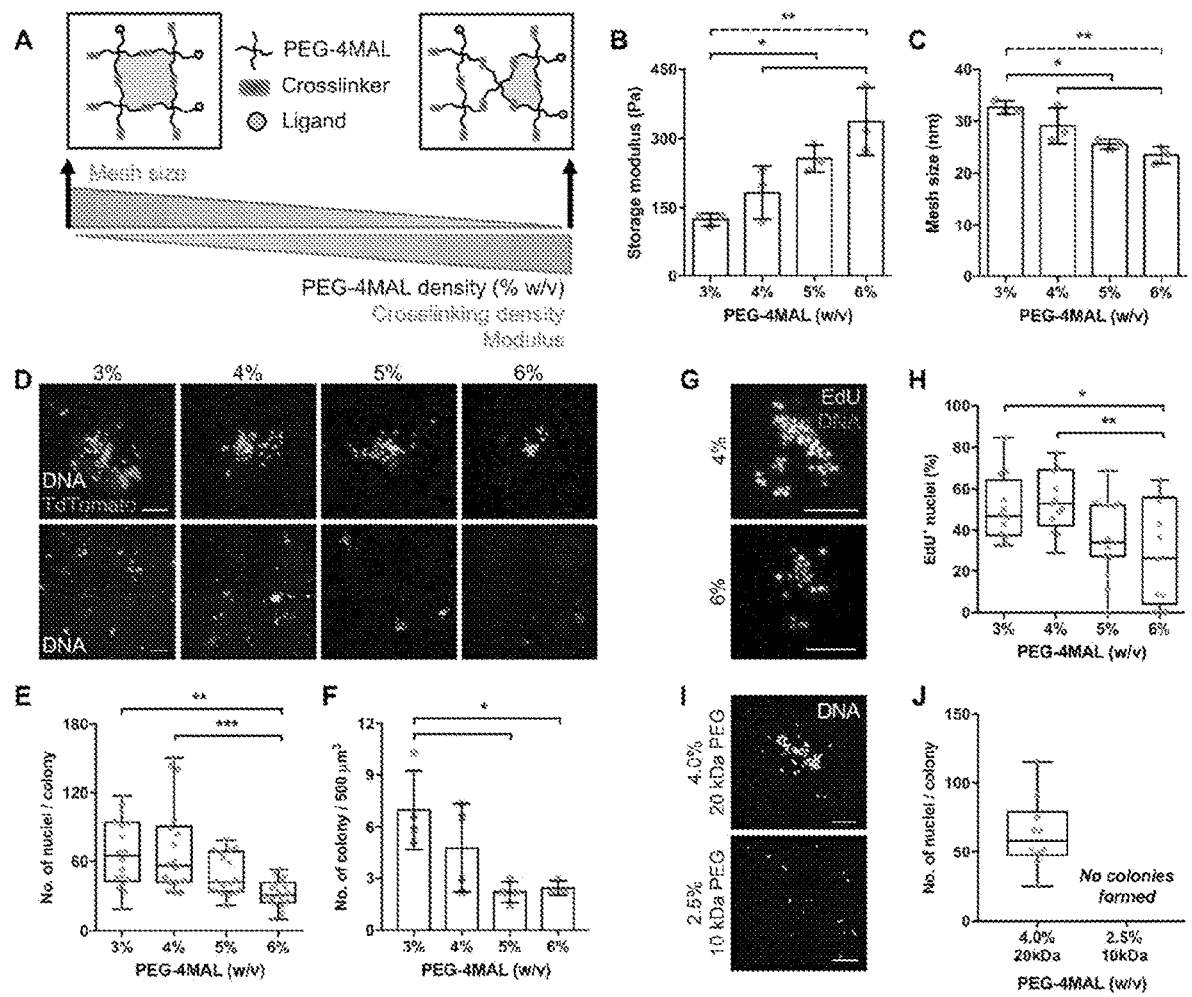
FIG. 2. PEG-4MAL macromer density modulates MuSC proliferation. (A) Schematic describing the changes in hydrogel mesh size and mechanical properties as a function of PEG-4MAL macromer density. (B) Storage modulus of hydrogels for different macromer densities. n=3 hydrogels. * p<0.05 (solid line), ** p<0.01 (dotted line) via 1-way ANOVA with Tukey's test. (C) Estimation of hydrogel mesh size based on the measured storage modulus. n=3 hydrogels. * p<0.05 (solid line), ** p<0.01 (dotted line) via 1-way ANOVA with Tukey's test. (D) Representative z-projections of myogenic colonies formed in PEG-4MAL hydrogels as a function of macromer density. Day 4. Top row scale bar: 100 µm. Bottom row scale bar: 250 µm. Percentage values indicate PEG-4MAL macromer density. (E-F) Quantification of myogenic colony (n=18 colonies) and density (n=3-4 hydrogels). * p<0.05,  p<0.01, * p<0.001 via 1-way ANOVA with Tukey's test. (G) Representative z-stack projections of EdU-labeled myogenic colonies. Day 4. Scale bar: 100 µm. (H) Quantification of EdU$^+$ nuclei. n=12-15 colonies. * p<0.05, ** p<0.01 via 1-way ANOVA with Tukey's test. (I) Representative Z-projections of MuSCs cultured in 4% 20 kDa and 2.5% 10 kDa PEG-4MAL hydrogels. Day 4. Scale bar: 100 µm. (J) Quantification of myogenic colonies. n=10 colonies. Bar graphs presented as mean±SD.

In the PEG-4MAL hydrogel system, the mechanical properties and mesh size can be modulated by altering the PEG-4MAL polymer density. As the polymer density increases (from 3 to 6% w/v), more crosslinks are introduced to the system resulting in formation of a tighter polymer network, and consequently, increased hydrogel storage modulus (from 150 to 300 Pa; FIGS. 2A and B). As tighter polymer networks are formed with increasing polymer density, the mesh size decreases (FIGS. 2A and C). To evaluate the effects of polymer density on MuSC function, freshly isolated MuSCs were encapsulated and cultured within 3%, 4%, 5%, and 6% 20 kDa PEG-4MAL hydrogels containing 1.0 mM RGD and crosslinked with protease-degradable peptides. MuSCs cultured in 3% and 4% PEG-4MAL hydrogels formed significantly larger myogenic colonies compared to cells in 6% PEG-4MAL hydrogels at day 4 ($p<0.01$ and $p<0.001$ respectively; FIGS. 2D and E). Furthermore, the number of colonies formed in 3% PEG-4MAL hydrogels was significantly greater compared to 5% and 6% PEG-4MAL hydrogels ($p<0.05$, FIGS. 2D and F). Finally, 3% and 4% PEG-4MAL hydrogels promoted significantly increased cell proliferation compared to 6% PEG-4MAL hydrogels ($p<0.05$ and $p<0.01$ respectively; FIGS. 2G and H), collectively indicating that 3-4% PEG-4MAL hydrogels support optimal MuSC proliferation and myogenic colony formation.

To determine the effects PEG-4MAL polymer density on MuSC activation, $Pax7^+/MyoD^+$ expression of MuSCs in 4% and 6% PEG-4MAL hydrogels presenting 1.0 mM RGD and crosslinked with protease-degradable peptides was examined at 76 hours post-encapsulation. Although no differences in MyoD expression were observed, myogenic colonies formed in 6% PEG-4MAL hydrogels exhibited significantly decreased levels of Pax7 expression compared to myogenic colonies formed in 4% PEG-4MAL hydrogels (FIGS. 10A and B).

To assess whether the increased cell proliferation with decreasing macromer density is an effect of mesh size or mechanical properties, MuSCs were encapsulated and cultured in 2.5% 10 kDa PEG-4MAL and 4% 20 kDa PEG-4MAL hydrogels, both presenting 1.0 mM RGD and crosslinked with protease-degradable peptides. The 2.5% 10 kDa PEG-4MAL hydrogels have decreased solute diffusivity compared to 4% 20 kDa PEG-4MAL hydrogels ($p<0.05$) due to the reduced molecular weight of the macromer, while exhibiting comparable mechanical properties ($p>0.05$) due to similar average crosslink density (FIG. 11A-F). MuSCs cultured in 2.5% 10 kDa PEG-4MAL did not form myogenic colonies on day 4 whereas colonies readily formed in 4% 20 kDa PEG-4MAL hydrogels (FIGS. 2I and J), suggesting mesh size imparts a significant impact on the proliferation capacity of MuSCs in a 3D-culture setting.

Matrix Degradability is Required for MuSC Function

Figure 3:
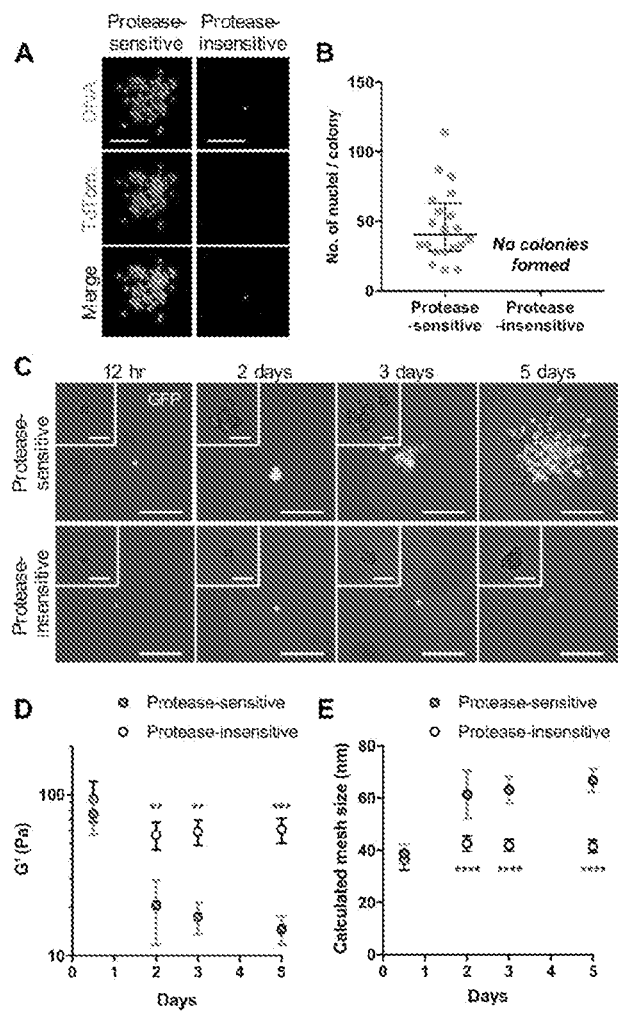
FIG. 3. Protease-degradability of the hydrogel is essential for MuSC proliferation. (A) Representative z-projections of MuSCs cultured in RGD-functionalized hydrogels synthesized with protease-sensitive and protease-insensitive cross-linkers. Day 4. Scale bar: 100 µm. (B) Quantification of myogenic colonies. Median±IQR. n=20. (C) Representative myogenic colony formation over time in protease-sensitive hydrogel and in protease-insensitive hydrogels over 5 days. Main scale bar: 50 µm. Inset scale bar: 10 µm. (D) Storage modulus and (E) mesh size of protease-sensitive and protease-insensitive hydrogels over 5 days.  p<0.01, * p<0.001, **** p<0.0001 vs time-matched protease-sensitive hydrogels via 2-way ANOVA with Sidak's test. n=4 hydrogels per time point. Mean±SD.

Extracellular matrix degradability is an important factor for dynamic remodeling of the cellular microenvironment. We hypothesized that the degradability of the synthetic PEG-4MAL hydrogel is a critical feature for MuSC function, including survival and proliferation. To test this hypothesis, we encapsulated freshly isolated $TdTomato^+$ MuSCs in RGD-functionalized 4% 20 kDa hydrogels crosslinked using either a protease-degradable peptide (GCRDVPMSMRGGDRCG; protease-sensitive) or protease-insensitive hexa(ethylene glycol) dithiol (protease-insensitive). MuSCs cultured in protease-degradable hydrogels formed robust myogenic colonies after 4 days in culture, whereas minimally viable MuSCs and no myogenic colonies were observed in the protease-insensitive hydrogels (FIGS. 3A and B). Indeed, a single MuSC encapsulated in protease-sensitive matrix readily degraded the surrounding matrix to proliferate and form a robust myogenic colony over time, whereas a MuSC in non-degradable, protease-insensitive matrix remained entrapped and unable to proliferate over time (FIG. 3C). Furthermore, the mechanical properties of protease-sensitive hydrogels containing MuSC declined with time in culture (FIG. 3D), and the calculated mesh size (FIG. 3E) increased over culture time. The mechanical properties and mesh size of MuSC-laden protease-insensitive cells remained relatively constant over time in culture. These results indicate that use of protease-degradable crosslinking peptides, which enable on-demand degradation of the cellular microenvironment, is essential for MuSC survival and proliferation in vitro within these synthetic niches.

Figure 4:
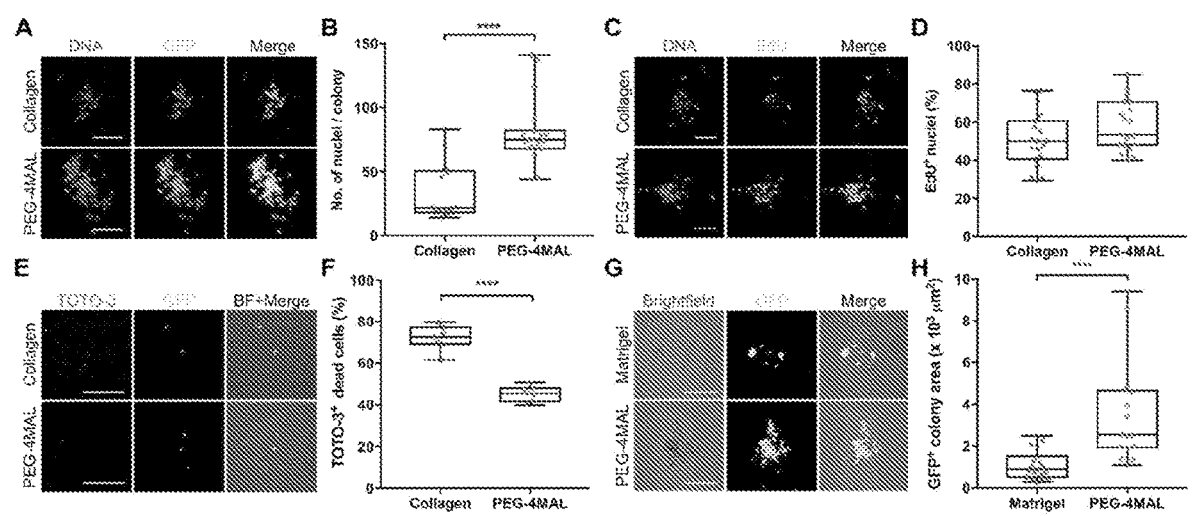
FIG. 4. Synthetic matrix supports higher MuSC proliferation potential than natural matrices. (A) Representative z-projections of myogenic colonies formed in 4% PEG-4MAL and 2.7 mg·ml$^{-1}$ collagen gels. Day 4. Scale bar: 100 µm. (B) Quantification of myogenic colony size. n=14-19 colonies. ** p<0.0001 via two-tailed Mann-Whitney U test. (C) Representative z-projections of EdU-labeled myogenic colonies formed in 4% PEG-4MAL and 2.7 mg·ml$^{-1}$ collagen gels. Day 4. Scale bar: 100 µm. (D) Quantification of EdU$^+$ nuclei. n=19 colonies. p=0.11 via unpaired two-tailed t-test. (E) Representative z-projections of GFP$^+$ MuSCs 1-day post-encapsulation in 4% PEG-4MAL and 2.7 mg·ml$^{-1}$ collagen gels. Scale bar: 100 µm. (F) Quantification of TOTO-3$^+$ dead MuSCs 1-day post-encapsulation. n=7 hydrogels.  p<0.0001 via unpaired two-tailed t-test. (G) Representative images of GFP$^+$ MuSCs 4-days post-encapsulation in 4% PEG-4MAL and Matrigel. Scale bar: 100 µm. (H) Quantification of GFP$^+$ myogenic colony area 4-days post-encapsulation. n=16-19 colonies. ** p<0.0001 via two-tailed Mann-Whitney U test.

Synthetic Matrix Supports Higher MuSC Proliferation Potential than Natural Matrices Collagen gels are commonly used as a natural extracellular matrix for cell culture in 3D. To determine how the engineered PEG-4MAL hydrogels perform in supporting MuSC function in comparison to collagen gels as a benchmark material, freshly isolated $GFP^+$ MuSCs were encapsulated in either RGD-functionalized 4% 20 kDa hydrogels crosslinked using protease-degradable peptides or 2.7 mg·ml$^{-1}$ type I collagen gels (storage modulus: 70±16 Pa). Myogenic colonies formed after 4 days of culture were significantly larger in the PEG-4MAL synthetic hydrogels compared to collagen gels ($p<0.0001$; FIGS. 4A and B). Despite the significant size differences in myogenic colonies formed in the PEG-4MAL hydrogels and collagen gels, no differences in cell proliferation were observed on day 4 of culture ($p>0.05$; FIGS. 4C and D). However, assessment of dead cells at 1 day post-encapsulation revealed that cell viability is significantly lower in collagen gels compared to the PEG-4MAL hydrogels ($p<0.0001$; FIGS. 4E and F, FIG. 12A). We attribute the larger myogenic colonies formed in the PEG-4MAL hydrogels to higher cell viability upon encapsulation. To eliminate potential effects of material stiffness on myogenic colony formation in 3D, MuSCs were cultured in either 2.7 mg·ml$^{-1}$ type I collagen gel or RGD-functionalized 2.8% 20 kDa PEG-4MAL hydrogels crosslinked with protease-degradable peptides, which exhibit similar storage modulus as 2.7 mg·ml$^{-1}$ type I collagen gel (FIG. 12B). Despite comparable mechanical properties, myogenic colonies formed in 2.8% PEG-4MAL hydrogels were significantly greater than colonies formed in 2.7 mg/ml collagen gel (FIG. S6C and D). This result suggests that other biophysical and biochemical differences, such as cell-binding site (type and density), material microstructure and function, and transport properties, regulate the differences in MuSC function between these biomaterial systems.

To assess MuSC function in comparison to Matrigel as an additional benchmark material, freshly isolated $GFP^+$ MuSCs were encapsulated in either RGD-functionalized 4% 20 kDa hydrogels crosslinked with protease-degradable peptides or Matrigel (storage modulus: 25.2±7.8 Pa). After 4 days of culture, significantly larger myogenic colonies were observed in the PEG-4MAL synthetic hydrogel compared to Matrigel ($p<0.0001$; FIGS. 4G and H). Furthermore, myogenic colonies formed Matrigel were morphologically rounder and closely clustered (FIG. 4G). Although Matrigel is an appropriate reference material, it is important to highlight limitations associated with Matrigel. Matrigel is generated from the Engelbreth-Holm-Swarm sarcoma that is rich in undefined extracellular matrix proteins. As a result, Matrigel is subjected to significant lot-to-lot variability in terms of composition and mechanical properties, and poses potential risk of pathogen transfer and immunogenicity, significantly limiting its clinical translation. Nonetheless, the results collectively demonstrate that the engineered synthetic matrix supports higher MuSC proliferation potential than collagen gels and Matrigel.

Synthetic Matrix Boosts Engraftment in Dystrophic Muscle Trauma

Acute muscle trauma imparts significant burden on the endogenous MuSC population to regenerate the damaged muscle, and the regenerative potential of muscle is further challenged when the normal mechanisms of muscle regeneration and homeostasis are chronically dysregulated. For instance, DMD muscles lacking dystrophin exhibit reduced mechanical integrity, and are prone to sarcolemma rupture upon repeated contraction.

Figure 5:
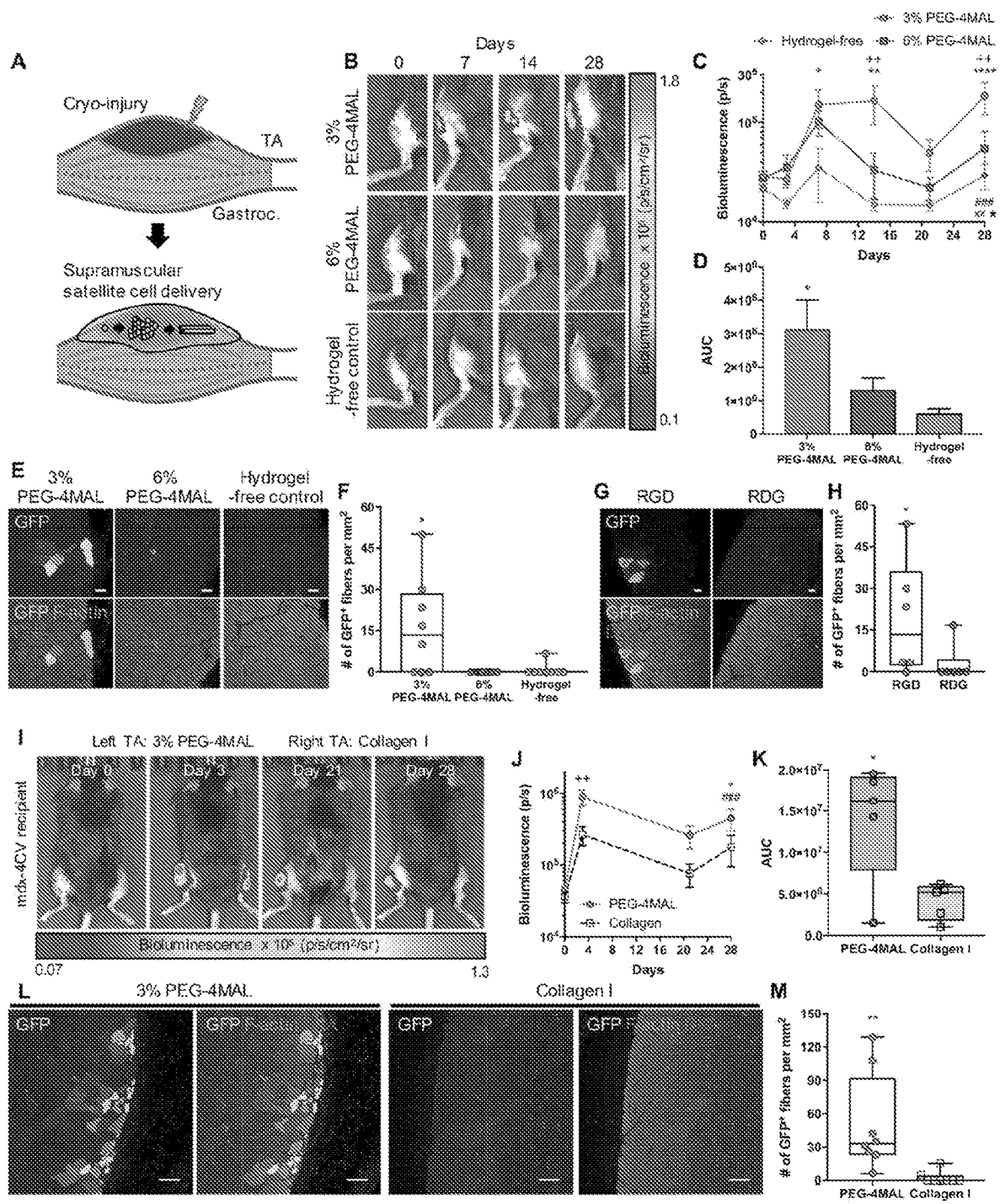
FIG. 5. Synthetic matrix enhances engraftment in dystrophic muscle trauma. (A) Schematic of injury and cell delivery. Cryo-injury was applied on the surface of TA muscle. Freshly isolated MuSCs were supramuscularly delivered in media (hydrogel-free) or encapsulated in hydrogel. (B) Representative IVIS images of mdx-4CV mouse hindlimbs treated with cell-laden 3% 20 kDa PEG-4MAL, 6% 20 kDa PEG-4MAL, or media. 12,500 MuSCs/TA. (C)

Moreover, dystrophin-deficient MuSCs exhibit abnormal mitosis and asymmetric division capacity, exacerbating the detrimental consequences of muscle injury. Transplantation of MuSCs stimulates muscle regeneration through cellular engraftment, however, cell delivery via direct injection poses several challenges at the translational level, including poor cell survival and limited applicability to traumatic injuries. To this end, we applied the bioengineered synthetic matrix to deliver MuSCs to the superficially injured tibialis anterior (TA) muscles of mdx-4CV mice, which exhibit chronic muscle degeneration and regeneration. We hypothesized that MuSCs delivered within the engineered PEG-4MAL hydrogel, which supports survival, activation, and proliferation, would migrate into the host muscle, resulting in enhanced cellular engraftment. Importantly, the PEG-4MAL hydrogel system enables in situ polymerization and direct integration to host tissue through thiol-presenting tissue and maleimide functional groups to improve in vivo cell retention and delivery, and thus provides a major advantage over other synthetic and natural materials. TA muscles of recipient mdx-4CV mice (13-19 weeks old) were injured by exposing the muscle surface to a liquid nitrogen-cooled probe prior to transplantation (FIG. 5A). A cryo-injury model was selected because it induces more localized injury compared to other commonly used models, such as cardiotoxin and notexin injections, through ablation of myofibers and mononuclear cells at the site of injury and necessitates MuSCs to migrate in from the non-injured sites. To evaluate the effects of PEG-4MAL polymer density on MuSC engraftment in vivo, freshly isolated β-actin $GFP^+$/luciferase$^+$ MuSCs encapsulated in 3% 20 kDa PEG-4MAL hydrogels containing 1.0 mM RGD, 6% 20 kDa PEG-4MAL hydrogels containing 1.0 mM RGD, or suspended in media (hydrogel-free) were delivered atop the injured TA muscles immediately after muscle injury (FIG. 5A). Both PEG-4MAL gels were crosslinked using protease-degradable peptides. The bioluminescence signal of MuSCs delivered in 3% PEG-4MAL hydrogels was elevated and sustained through day 28 post-transplantation compared to hydrogel-free condition ($p<0.01$ over time, $p<0.05$ on day 28; FIGS. 5B and C). Analysis of the area under the bioluminescence curve further substantiated this observation ($p<0.05$; FIG. 5D). Indeed, MuSCs delivered in 3% PEG-4MAL hydrogels successfully differentiated and formed $GFP^+$ fibers, whereas MuSCs delivered in 6% PEG-4MAL hydrogels or media alone did not engraft ($p<0.05$; FIGS. 5E and F). Collectively, the results indicate that MuSCs delivered in 3% PEG-4MAL hydrogels directly on top of acutely injured dystrophic TA muscles support in vivo retention, survival and proliferation, and promote cellular engraftment into the injured host muscle.

We next examined the importance of the RGD adhesive peptide in the delivery hydrogel vehicle on MuSC engraftment. $GFP^+$ MuSC transplantation efficacy using 3% PEG-4MAL hydrogels crosslinked with protease-sensitive peptides and functionalized with either 1.0 mM RGD or 1.0 mM scrambled RDG were compared in the cryo-injured TA muscles of mdx-4CV mice. Significantly higher number of $GFP^+$ fibers were observed in the RGD-presenting hydrogel group compared to the scrambled RDG-presenting hydrogel group on day 28 post-transplantation ($p<0.05$; FIGS. 5G and H).

To directly compare MuSC transplantation efficacy of the engineered PEG-4MAL hydrogels to collagen gels, the bioluminescence signal of MuSCs delivered to injured muscle using either RGD-presenting 3% PEG-4MAL hydrogels crosslinked with protease-sensitive peptides or 2.7 mg·ml$^{-1}$ collagen gels was monitored over time. MuSCs delivered using the PEG-4MAL hydrogels exhibited significantly higher overall bioluminescence signal compared to collagen over the course of 28 days ($p<0.05$; FIGS. 5I and J). Further analysis of the area under the bioluminescence curve substantiated that MuSCs delivered using PEG-4MAL hydrogels resulted in significantly higher engraftment than MuSCs delivered using collagen gels ($p<0.05$; FIG. 5K), indicating superior performance of the PEG-4MAL hydrogel compared to collagen gels for delivery of MuSCs to injured TA muscles.

The engraftment potential is strongly dependent on the number of MuSCs delivered. To demonstrate the feasibility of achieving higher number of engrafted fibers using the engineered PEG-4MAL hydrogels, approximately 50,000 freshly isolated $GFP^+$ MuSCs were delivered to the cryo-injured TA muscles of mdx-4CV mice. Delivery of MuSCs in 3% PEG-4MAL hydrogels resulted in robust engraftment 28 days post-transplantation, where the mean number of $GFP^+$ fibers increased significantly (~15 to 50 fibers/mm$^2$) by increasing the donor cell quantity (FIGS. 5L and M). Delivery of MuSCs using collagen gel resulted in minimal engraftment (FIGS. 5L and M), further demonstrating the efficacy of the engineered PEG-4MAL hydrogels.

Synthetic Matrix Boosts MuSC Engraftment in Aged Muscle Trauma

Aged skeletal muscles exhibit impaired regenerative capacity upon injury. To confirm that aged muscles display diminished regeneration upon superficial cryo-injury compared to young muscles, young (4 months old) and aged (22 months old) muscles were subjected to cryo-injury as described above, and their native endogenous regeneration was assessed. Young (4 months old) TA muscle regenerated to tissue comparable to native uninjured TA by day 14 post-injury, whereas aged (22 months old) TA muscle did not completely regenerate by day 14 post-injury, as indicated both by the smaller fiber cross-sectional area and higher presence of centrally-localized myonuclei ($p<0.0001$; FIGS. 6A and B). To test whether the engineered PEG-4MAL hydrogel can also promote MuSC engraftment in injured aged muscle, freshly isolated β-actin $GFP^+$/luciferase$^+$ MuSCs encapsulated in 3% 20 kDa PEG-4MAL hydrogels containing 1.0 mM RGD and crosslinked with protease-degradable peptides or suspended in media (hydrogel-free) were delivered to the supramuscular locus of the cryo-injured TA muscles of aged mice (23 months old). Delivery of MuSCs using the PEG-4MAL hydrogel resulted in a progressive increase in the bioluminescence signal up to 7 days post-transplantation, and this signal was sustained through day 28 post-transplantation (FIGS. 6C and D). In contrast, MuSCs delivered without the hydrogel resulted in no change in bioluminescence signal over time, and this signal was significantly lower than the signal for the hydrogel group ($p<0.05$; FIG. 6C-E). Consistent with these results, increased numbers of $GFP^+$ fibers, indicative of transplanted cell engraftment, were observed for muscles treated with MuSCs delivered within PEG-4MAL gels whereas no GFP+ fibers were seen for muscles treated with MuSCs without the hydrogel carrier (FIG. 6F). These results show that PEG-4MAL hydrogel promotes donor MuSC retention, survival, proliferation, and engraftment in injured aged muscle.

Example 2: Preparation and Evaluation of MuSC and/or Wnt7a Loaded Hydrogels Animals All live animal procedures were conducted under the approval of the Institutional Animal Care and Use Committee of the Georgia Institute of Technology. Mice were housed, maintained, and bred in the Physiological Research Laboratory Animal Facility of the Georgia Institute of Technology. C57Bl/6 and mdx (B6Ros.Cg-DMD$^{mdx-4CV}$/J) mice were obtained from the Jackson Laboratory. CAG-luc-Ka-β-actin-EGFP mice were generated by crossing C57Bl/6-β-actin-EGFP (kindly provided by Amy Wagers, Harvard University) and FVB-Tg(CAG-luc,-GFP)L2G85Chco/J (acquired from the Jackson Laboratory) mice. These mice were backcrossed for more than 5 generations and maintained in C57Bl/6 background. Both male and female mice were used in a randomized manner.

Synthesis of Wnt7a-Loaded Hydrogel

Four-arm PEG-4MAL macromer (20 kDa, Laysan Bio) was reconstituted in 1× phosphate-buffered saline (PBS) containing 10 mM HEPES (pH 7.4). Cell adhesive peptides (GRGDSPC, or scrambled GRDGSPC; >95% purity; GenScript) were dissolved in PBS containing 10 mM HEPES. To generate peptide-functionalized PEG-4MAL precursors, cell adhesive peptides were mixed with the PEG-4MAL solution. Subsequently, recombinant human Wnt7a (R&D systems) reconstituted in PBS was added to the PEG-4MAL precursor solution. To synthesize Wnt7a-loaded hydrogel, protease-degradable cross-linking peptide (GCRDVPMSMRGGDRCG; >95% purity; GenScript) dissolved in PBS containing 10 mM HEPES was mixed with the PEG-4MAL precursor solution containing Wnt7a and polymerized at 37° C. for 5 minutes.

Release Assay

Wnt7a was labeled with AlexaFluor 488 NHS ester (ThermoFisher Scientific) per the manufacturer's instructions. 1 μg labeled-Wnt7a was encapsulated in a 15 μL PEG-4MAL hydrogel and subsequently submerged in 1 mL PBS. Release kinetics of Wnt7a from hydrogels was fluorescently quantified over time at 37° C. by sampling the bathing solution in a 24-well microvolume microplate and SpectraMax M3 reader (Molecular Devices). For each time point, PBS (blank control) and free 1 μg labeled-Wnt7a in 1 mL PBS (100% control) were also assayed. To degrade Wnt7a-loaded hydrogels, the hydrogels were incubated in collagenase I (3.9 U/mL in PBS; Worthington Biochemical Corporation) at 37° C.

In Vitro Bioactivity Assay

C2C12 myoblasts were cultured in 1.5 mL growth media (Dulbecco's modified Eagle's medium, DMEM containing 100 U/mL penicillin/streptomycin and 10% fetal bovine serum [FBS]) in 12-well plates until confluency. Subsequently, the growth media was replaced with 1.5 mL of differentiation media (DMEM containing 100 U/mL penicillin/streptomycin and 2% horse serum) containing Wnt7a (75 ng)-loaded PEG-4MAL hydrogels (4%, 6%, 8% w/v), free Wnt7a (75 ng), or PBS control. After 5 days of differentiation, myotubes were fixed using 4% paraformaldehyde for 20 minutes at room temperature, washed, treated with blocking/permeabilizing buffer (2% bovine serum albumin [BSA], 0.5% goat serum, and 0.5% Triton X-100 in PBS), and stained for myosin heavy chain (1:200; MF20, Developmental Studies Hybridoma Bank) overnight at 4° C. The myotubes were washed 3 times using PBS containing Tween-20 (0.1% v/v) and incubated with AlexaFluor 488-conjugated goat anti-mouse IgG (1:250; ThermoFisher) for 1 hour at room temperature. Samples were washed 3 times using PBS containing Tween-20 (0.1% v/v) and imaged using an epi-fluorescent microscope (Zeiss Observer D1). To assess the degree of hypertrophy, myotube diameters were measured using Fiji ImageJ 1.52e.

PEG-4MAL Macromer Muscle Adhesion Assay

Scrambled RDG peptides (GRDGSPC; >95% purity; GenScript) were labeled with DyLight 755 NHS ester (ThermoFisher Scientific) per the manufacturer's instructions. DyLight 755-labeled RDG-functionalized PEG-4MAL precursors (remaining maleimide concentration=$6.27\times10^{-3}$ mol/mL) were produced as described above. To generate maleimide-quenched precursors, excess L-cysteine (Millipore Sigma) dissolved in PBS was added to the PEG-4MAL solution. 15 μL of PBS, macromer solution with quenched maleimides, or macromer solution with reactive maleimides was pipetted onto the TA surfaces of freshly sacrificed mdx-4CV mice. Treated TA muscles were harvested and washed for 5 min twice in PBS. Fluorescence measurement of the TAs was acquired using the IVIS SpectrumCT in vivo imaging system (PerkinElmer).

MuSC Isolation

Hindlimb muscles from 2-4-month-old mice were minced and digested in DMEM containing collagenase type II (0.2%; Worthington Biochemical Corporation) and dispase II (2.5 U/mL; Thermo Fisher) for 90 min at 37° C. on a shaker. The muscle digest was triturated every 30 min using an FBS-coated serological pipette. Upon digestion, the muscle digest was diluted by adding a two-part volume of 20% FBS in F10 media. The resulting solution was filtered through a 70 μm cell strainer. Cell pellets were obtained by centrifuging (300 g) the solution for 5 min at 4° C. The cell pellets were retrieved by removing supernatant and further washed using 2% FBS in Hank's balanced salt solution (HBSS) through 5 min centrifugation (300 g) at 4° C. To stain the cells with primary antibodies, a cocktail of primary antibodies (1:100) was added to the cell suspension solution in 2% FBS in HBSS and incubated for 30 min on ice. The primary antibody cocktail consists of phycoerythrin (PE)-conjugated anti-mouse CD29 (13.3%; BioLegend), allophycocyanin (APC)-conjugated anti-mouse Sca1 (13.3%; BioLegend), CD45 (13.3%; BioLegend), CD11b (13.3%; BioLegend), CD31 (13.3%; BioLegend), Ter119 (13.3%; BioLegend), and biotinylated anti-mouse CD184 (20.2%; BD Pharmingen). The cells were washed in 2% FBS in HBSS through 5 min centrifugation (300 g) at 4° C. The cells were further incubated with streptavidin PE-Cy7 (1:100; eBioscience) for 20 min on ice and washed as described above. Immediately before cell sorting, propidium iodide (1:1000; ThermoFisher) was added to the cell solution. Propidium iodide$^-$, CD29$^+$, CD184$^+$, Sca1$^-$, CD31$^-$, CD45$^-$, CD11b$^-$, Ter119$^-$ MuSCs were sorted via fluorescence-activated cell sorting (BD FACSAria III Cell Sorter).

3D MuSC Culture, Proliferation, and Migration Assay

Freshly isolated MuSCs were encapsulated in 4% 20 kDa PEG-4MAL hydrogels (1.0 mM RGD, with or without 50 ng/mL Wnt7a, VPM crosslinked) as described above. MuSCs were cultured in growth media (F10 containing 100 U/mL penicillin/streptomycin, 1× GlutaMAX, and 20% horse serum). For EdU staining, cells were incubated in 10 μM EdU-containing growth media for 5 hours. Subsequently, the cells were fixed in 4% paraformaldehyde for 20 min at room temperature and washed three times using PBS. The cells were blocked and permeabilized using PBS containing 2% BSA, 0.5% goat serum, and 0.5% Triton X-100 for 1 hour at room temperature. EdU detection was conducted per the manufacturer's instructions (Thermo Fisher). Cell nuclei were stained with Hoechst (1:1000) prior to z-stack imaging using a confocal microscope (Nikon Eclipse Ti-E C2+). The number of nuclei and EdU$^+$ nuclei were automatically counted using CellProfiler. Total colony area per volume was quantified using ImageJ. To assess MuSC migration, 4% 20 kDa PEG-4MAL hydrogels (1.0 mM RGD, VPM crosslinked) containing Wnt7a (50 ng) or PBS were cast in angiogenesis plate wells (ibidi), and freshly isolated 10,000 GFP$^+$ MuSCs were seeded on top of the hydrogels. 1,360 µm-thick z-stack projections were taken, from the top of the hydrogel, using a confocal microscope (Nikon Eclipse Ti-E C2$^+$). Cell migration distance was quantified using ImageJ.

Freeze Injury and Wnt7a/MuSC Delivery

Mice were anesthetized by inhalation of 2.5% isoflurane. Sustained-release buprenorphine (0.8 mg/kg) was subcutaneously administered immediately after induction. The hindlimb hair was depilated to expose the skin. To expose the TA muscle, an incision was made through the skin and fascia between the TA and gastrocnemius muscles on the lateral side. A liquid nitrogen-cooled metal probe (#5 hex key) was positioned on the TA surface for 10 sec to induce freeze injury. Approximately 45 seconds after inducing the freeze injury (muscle turns from white to pink), 15 µL of unpolymerized PEG-4MAL hydrogel solution (4% 20 kDa PEG-4MAL, 1.0 mM RGD, VPM crosslinking peptide; G' 182.6±57.2 Pa, G" 12.5±3.3 Pa containing 2.5 µg Wnt7a or PBS was cast on the freeze-injured TA of C57Bl/6J mice using a P20 micropipette. The hydrogel was formulated to polymerize within 5 seconds upon contact with the muscle surface. These animals were euthanized on day 14 post-treatment. For hydrogel-mediated co-delivery of Wnt7a and freshly isolated GFP$^+$ MuSCs (in C57Bl/6J background), 15 µL PEG-4MAL hydrogel (3% 20 kDa PEG-4MAL, 1.0 mM RGD, VPM crosslinked; G' 124.2±13.7 Pa, G" 8.17±1.6 Pa, previously reported in containing 300 ng Wnt7a with MuSCs or PBS with MuSCs was cast on the injured TA of mdx mice immediately upon freeze-injury application. The skin incision was closed using degradable surgical suture (Vicryl suture, Ethicon). These animals were euthanized on day 28 post-treatment. All procedures were conducted using aseptic techniques.

Tissue Histology and Immunostaining

Hindlimbs were fixed in 4% paraformaldehyde for 1 hour at room temperature. Fixed hindlimbs were washed in PBS three times and incubated in 20% sucrose (w/v in PBS) overnight at 4° C. Dissected TA muscles were frozen in liquid nitrogen-cooled 2-methylbutane. 10 µm-thick tissue sections were acquired through cryo-sectioning. Prior to tissue staining, the sectioned tissues were treated with blocking/permeabilizing buffer (2% BSA, 0.5% goat serum, and 0.5% Triton X-100 in PBS) for 1 hour at room temperature.

To stain for Pax7, TA muscles were frozen unfixed. 10 µm-thick tissue sections were obtained and fixed using 4% paraformaldehyde for 8 min. Heat activated antigen retrieval was performed by incubating the tissues in citrate buffer (pH 6.0) and treating in a high-pressure cooker for 10 min. The tissue sections were washed using PBS, blocked using blocking/permeabilizing buffer (2% BSA, 0.5% goat serum, and 0.5% Triton X-100) for 1 hour at room temperature, and finally incubated in blocking/permeabilizing buffer containing AffiniPure Fab goat anti-mouse-IgG (1:25; Jackson ImmunoResearch Laboratories, Inc.) for 1-2 hours at room temperature The following primary and secondary antibodies were used to stain tissue sections in this study: rabbit polyclonal anti-dystrophin (1:200; Abcam), Pax7 (1:80, Developmental Studies Hybridoma Bank), Alexa Fluor 488-conjugated anti-GFP (1:250; ThermoFisher), Alexa Fluor 555 goat anti-mouse IgG (1:250; ThermoFisher), Alexa Fluor 488 goat anti-rabbit IgG (1:250; ThermoFisher). Hoechst 33342 (1:1000; Thermo Fisher) was used to counterstain cell nuclei.

Pax7$^+$ MuSC and Myofiber Cross-Sectional Area Quantification

To quantify Pax7$^+$ MuSCs, tissue sections were imaged and manually quantified in a blinded manner, where the slide labels were physically masked using a nontransparent tape by a different researcher who did not partake in the imaging and quantification process. The number of Pax7$^+$ MuSCs were scored from 8 images per muscle. Myofiber cross-sectional area was automatically quantified using ImageJ. Briefly, the dystrophin images were converted 8-bit and automatic threshold was applied. Myofiber cross-sectional areas were then automatically quantified using the Analyze Particle function.

Statistical Analyses

Statistical tests were conducted using GraphPad Prism 8. Normality was tested using the Shapiro-Wilk test. Two-way repeated measures ANOVA with Tukey's multiple comparisons tests were performed on the Wnt7a release data. Two-way ANOVA with Sidak's multiple comparisons tests was performed to myogenic colony formation and EdU incorporation assay data. For all other multiple group comparisons, one-way ANOVA with Tukey's tests or Kruskal-Wallis test with Dunn's tests were performed based on data normality. For the paired comparisons, two-tailed paired t-tests were conducted. Two-tailed unpaired t-tests were performed for all other two-group comparisons. Significance levels were set at *$p<0.05$, $p<0.01$, *$p<0.001$, ****$p<0.0001$.

Results

The Wnt7a release rate can be modulated by encapsulating in PEG-4MAL hydrogels with different polymer densities. The release rate of Wnt7a through passive diffusion is significantly delayed in 8% (w/v) PEG-MAL hydrogel compared to 6% PEG-4MAL hydrogel (FIG. 13b; $p<0.0001$) in the absence of collagenase; this result is expected based on the tighter network mesh for the higher polymer density gels. The release rate of Wnt7a is further increased in presence of protease (i.e., 3.9 U/mL of collagenase type I; FIG. 13b; $p<0.0001$), indicating that the release rate can be further enhanced through proteolytic degradation of the hydrogel.

To determine whether hydrogel-released Wnt7a retains its bioactivity, we assessed the capacity of hydrogel-released Wnt7a to promote in vitro myotube hypertrophy (FIG. 14a). In differentiated myotubes, Wnt7a binds to Fzd7 and activates the Akt/mTOR protein synthesis pathway to induce myotube hypertrophy as characterized by an increase in the myotube diameter distribution. Significant hypertrophy of C2C12 myotubes was observed with treatment with free Wnt7a (FIG. 14b, c, g; $p<0.05$) compared to PBS control. Treating C2C12 myotubes with Wnt7a-releasing 4% PEG-4MAL hydrogel resulted in a comparable degree of hypertrophy as free Wnt7a (FIG. 14c, d, g; $p>0.05$). Treatment with Wnt7a-loaded 6% and 8% PEG-4MAL hydrogels resulted in decreased levels of myotube hypertrophy, compared to both free Wnt7a and 4% PEG-4MAL conditions (FIG. 14c, d, e, f, g; p<0.05). The distribution of myotube diameter increased with decreasing hydrogel polymer density (FIG. 14h), further suggesting that the effect of delivered Wnt7a can be temporally modulated by altering the Wnt7a release kinetics (FIG. 13b). Collectively, these data indicate that hydrogel-released Wnt7a retains its bioactivity in vitro. Engineered PEG-4MAL Hydrogel Enables Effective Local Delivery of Wnt7a to the Injured Skeletal Muscle The PEG-4MAL hydrogel can adhere to the tissue through maleimide-thiol interactions at physiologic conditions, and thus offers a unique advantage for locally administering therapeutics at the site of tissue injury where direct injections are not practical (FIG. 15a). Indeed, retention of unpolymerized, reacting PEG-4MAL macromers on the surface of TA muscle is significantly higher compared to unpolymerized macromers with quenched maleimides (p<0.05) and untreated (p<0.01; FIGS. 15b and c), corroborating the feasibility of adhering a Wnt7a-loaded PEG-4MAL hydrogel to skeletal muscle. Thus, this system offers an opportunity to deliver Wnt7a as a "patch" to enhance muscle regeneration in traumatic muscle injury where direct injections may not be feasible.

To further assess the feasibility of promoting muscle regeneration by locally administering Wnt7a in severe muscle injury, we delivered Wnt7a-loaded hydrogels to the supramuscular locus of injured TA (immunocompetent C57Bl/6J mice) immediately upon freeze injury application. The freeze-injury model is a well-established physical surface injury mode and offers a robust proof-of-concept injury model for evaluating cell/protein-based therapeutics delivery across the biomaterial-tissue boundary. By day 14 post-treatment, the muscles treated with Wnt7a-loaded hydrogels exhibited significantly increased median myofiber area at the site of injury compared to the muscles treated with Wnt7a-free hydrogels (FIGS. 16a and b; p<0.05). Treatment with Wnt7a-loaded hydrogels also significantly increased TA mass compared to TAs treated with Wnt7a-free control hydrogels (FIG. 16c; p<0.01). Furthermore, a significantly higher number of endogenous Pax7$^+$ MuSCs were found in the TAs treated with Wnt7a-loaded hydrogels compared to control gels (FIGS. 16d and e; p<0.05). Collectively, these results suggest that hydrogel-release Wnt7a retains its bioactivity in vivo, and that local delivery of Wnt7a to severely injured muscle using the engineering PEG-4MAL hydrogel is feasible and effective in accelerating muscle regeneration.
Wnt7a Promotes MuSC Migration Through the Engineered PEG-4MAL Hydrogel Wnt7a promotes symmetric expansion and migration of MuSCs through the planar cell polarity pathway involving Dvl2 and the small GTPase Rac1. Furthermore, a brief treatment of MuSCs prior to transplantation enhances engraftment, supporting the application of hydrogel-mediated MuSCs transplantation with Wnt7a to treat muscle trauma. We have previously engineered a PEG-4MAL hydrogel that is conducive to primary MuSC function and demonstrated that MuSC transplantation using the engineered hydrogel significantly improves the engraftment potential. To determine how Wnt7a influences MuSC proliferation within the engineered hydrogel in vitro, we encapsulated freshly isolated MuSCs in hydrogels presenting either RGD or RDG (scrambled inactive control) integrin-targeting ligands with or without Wnt7a. Myogenic colonies formed in the RGD-presenting hydrogel were significantly larger than the colonies formed in the RDG-presenting hydrogels (FIGS. 17a and b; p<0.001). However, encapsulated Wnt7a did not result in an increased size of myogenic colony formation in both RGD- and RDG-functionalized hydrogels (FIGS. 17a and b). Although no significant difference in EdU incorporation was observed within the RGD-presenting gels with encapsulated Wnt7a, the number of EdU$^+$ nuclei per colony in the Wnt7a-treated RGD-presenting hydrogel was significantly higher than both RDG-functionalized conditions (FIGS. 17a and c; p<0.01). Furthermore, no difference in colony density was observed in RGD-presenting hydrogels with encapsulated Wnt7a compared to control RGD-presenting gels (FIGS. 17d and e), indicating that Wnt7a does not increase the proliferation capacity of myogenic progenitors in the engineered PEG-4MAL hydrogel. However, MuSCs seeded on top of Wnt7a-releasing hydrogel exhibited increased invasion distance into the hydrogel compared to MuSCs seeded on Wnt7a-free hydrogel (FIGS. 17f and g). This result shows that Wnt7a promotes MuSCs migration through the engineered synthetic matrix, which could further improve transplantation efficacy when delivered to the injured muscle in vivo.
Wnt7a Promotes MuSC Migration In Vivo Next, we sought to evaluate the feasibility of simultaneous MuSC and Wnt7a delivery using the engineered PEG-4MAL hydrogel as a "patch" in skeletal muscle conditions where direct injections are not feasible. Importantly, topical delivery of MuSCs using the engineered PEG-4MAL hydrogel to the supramuscular locus of freeze-injured TA muscle (immunocompetent mdx mice) significantly increases engraftment potential compared to the hydrogel-free condition (FIGS. 18a and b; day 28 post-transplantation), demonstrating that the engineered PEG-4MAL hydrogel is required for successful transplantation of MuSCs delivered in this manner. To further evaluate the effect of Wnt7a on MuSC engraftment, we next delivered freshly isolated GFP$^+$ MuSCs using the engineered PEG-4MAL hydrogels with or without encapsulated Wnt7a to the supramuscular locus of freeze-injured TA (immunocompetent mdx mice) muscles. Transplantation of MuSCs via the engineered PEG-4MAL hydrogel containing Wnt7a did not increase the number of GFP$^+$ fibers engrafted (FIGS. 6c and d; p>0.05; day 28 post-transplantation). However, the minimal distance of GFP$^+$ engrafted fibers from the TA surface was significantly increased when MuSCs were co-delivered with Wnt7a via the PEG-4MAL hydrogel (FIGS. 18c and e), suggesting that MuSCs delivered in the absence of Wnt7a preferentially engraft along the supramuscular locus, while MuSCs co-delivered with Wnt7a engraft at a deeper location from the TA surface and the delivery site. Taken together, the data demonstrate that co-delivery of MuSCs and Wnt7a to the supramuscular locus of injured TA muscle using the engineered PEG-4MAL hydrogel promotes MuSC in vivo migration without impacting the engraftment efficiency.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:
1. A method of repairing muscle tissue in a human patient in need thereof, comprising:
forming micropunctures on the muscle tissue with a substrate comprising microneedles;
wherein the muscle tissue is diaphragm muscle tissue;
wherein the patient has muscular dystrophy;
contacting the muscle tissue having micropunctures with a composition comprising a pro-myogenic agent dispersed in a hydrogel matrix, wherein the hydrogel matrix comprises a crosslinked hydrophilic polymer network covalently bonded to a plurality of adhesion peptides;
wherein the crosslinked hydrophilic polymer network has the general formula:

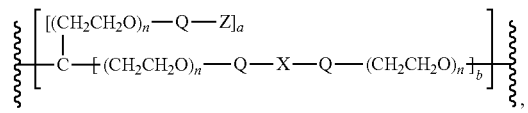

wherein C represents a core, n is an integer from 20-2,000, Q is a linking moiety, Z is an adhesion peptide, X is a crosslinker, a is greater than 0 and b is greater than 1, provided the sum of a+b does not exceed 7;
wherein C represents a group having the formula:

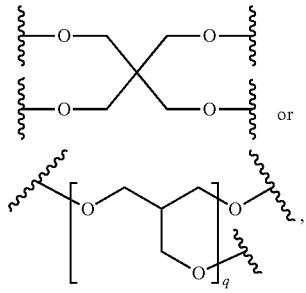

wherein q is from 1-6;
Q represents a group having the formula:

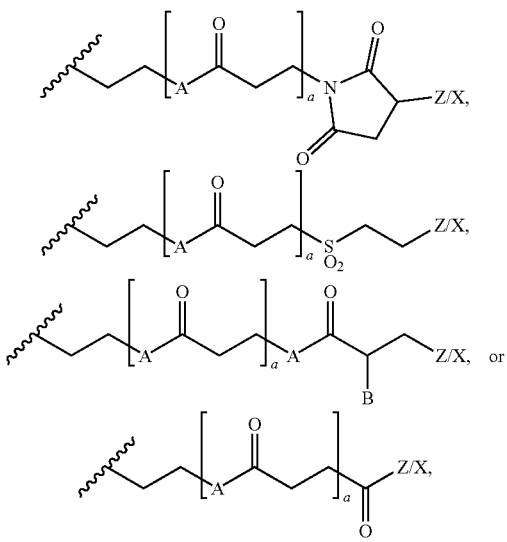

wherein A is independently selected from O or NH, a is independently selected from 0 or 1, B is selected from hydrogen or methyl, and Z/X in each case independently represents either an adhesion peptide or crosslinker;
wherein the pro-myogenic agent comprises muscle stem cells and/or satellite cells, wherein the pro-myogenic agent further comprises a pro-myogenic protein comprising Wnt7a, FGF2, VEGF, IGF-1, GDNF, MG53, or a combination thereof;
wherein the adhesion peptide comprises the sequence GRGDSPC (SEQ ID NO: 1), CRGDS (SEQ ID NO: 2), CRGDSP (SEQ ID NO: 3), CPHSRN (SEQ ID NO: 4), CGWGGRGDSP (SEQ ID NO: 5), CGGSIDQVEPYSSTAQ (SEQ ID NO: 6), CGGRNIAEIIKDI (SEQ ID NO: 7), CGGDITYVRLKF (SEQ ID NO: 8), CGGDITVTLNRL (SEQ ID NO: 9), CGGRYVVLPR (SEQ ID NO: 10), CGGKAFDITYVRLKF (SEQ ID NO: 11), CGGEGYGEGYIGSR (SEQ ID NO: 12), CGGATLQLQEGRLHFXFDLGKGR, wherein X=Nle (SEQ ID NO: 13), CGGSYWYRIEASRTG (SEQ ID NO: 14), CGGGEFYFDLRLKGDKY (SEQ ID NO: 15), CKGGNGEPRGDTYRAY (SEQ ID NO: 16), CKGGPQVTRGDVFTMP (SEQ ID NO: 17), CGGNRWHSIYITRFG (SEQ ID NO: 18), CGGASIKVAVSADR (SEQ ID NO: 19), CGGTTVKYIFR (SEQ ID NO: 20), CGGSIKIRGTYS (SEQ ID NO: 21), CGGSINNNR (SEQ ID NO: 22), CGGSDPGYIGSR (SEQ ID NO: 23), CYIGSR (SEQ ID NO: 24), CGGTPGPQG (SEQ ID NO: 25), CGGTPGPQGIAGQRVV (SEQ ID NO: 26), CGGMNYYSNS (SEQ ID NO: 27), CGGKKQRFRHRNRKG (SE ID NO: 28), CRGDGGGGGGGGGGGGPHSRN (SEQ ID NO: 29), CPHSRNSGSGSGSGGRGD (SEQ ID NO: 30), Acetylated-GCYGRGDSPG (SEO ID NO: 31), ((GPP)5GPC) (SEQ ID NO: 32), CRDGS (SEX ID NO: 33), cyclic RGD{Fd}C (SEQ ID NO: 34), CGGRKRLOVOLSIRT (SEQ ID NO: 35), CIKVAV (SEQ ID NO: 36), CGGAASIKVAVSADR (SEQ ID NO: 37), CGGKRTGQYKL (SEQ ID NO: 38), CGGTYRSRKY (SEQ ID NO: 39), CGGYGGGP(GPP)5GFOGERPP(GPP)4GPC (SEQ ID NO: 40), CGGKRTGQYKLGSKTGPGQK (SEQ ID NO: 41), QAKH KQRKRLKSSC (SEQ ID NO: 42), SPKH HSQRARKKKNKNC (SEQ ID NO: 43), CGGXBBXBX, wherein B=basic residue and X=hydropathic residue (SEQ ID NO: 44), and CGGXBBBXXBX, wherein B=basic residue and X=hydropathic residue (SEQ ID NO: 45), or a combination thereof; and
the crosslinker comprises a peptide having the sequence GCRDGPQG↓IWGQDRCG (SEQ ID NO: 46), GCRDGPQG↓IAGQDRCG (SEQ ID NO: 47), GCRDVPMS↓MRGGDRCG (SEQ ID NO: 48), GCRDIPVS↓LRSGDRCG (SEQ ID NO: 49), GCRDRPFS↓MIMGDRCG (SEO ID NO: 50), GCRDVPLS↓LTMGDRCG (SEO ID NO: 51), GCRDVPLS↓LYSGDRCG (SEQ ID NO: 52), GCRDIPES↓LRAGDRCG (SEQ ID NO: 53), GCRDSGESPAY↓YTADRCG (SEQ ID NO: 54), GCRDGGYAE↓LRMGGDRCG (SEQ ID NO: 55), GCRDGGPLG↓LYAGGDRCG (SEQ ID NO: 56), or GCRDGPLG↓LWARDRCG SEQ ID NO: 57), 1,4-dithiothreitol poly(ethylene glycol) dithiol, or a combination thereof.

2. The method according to claim 1, wherein C represents a group having the formula:

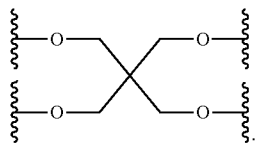

3. The method according to claim 1, wherein Q represents a group having the formula:

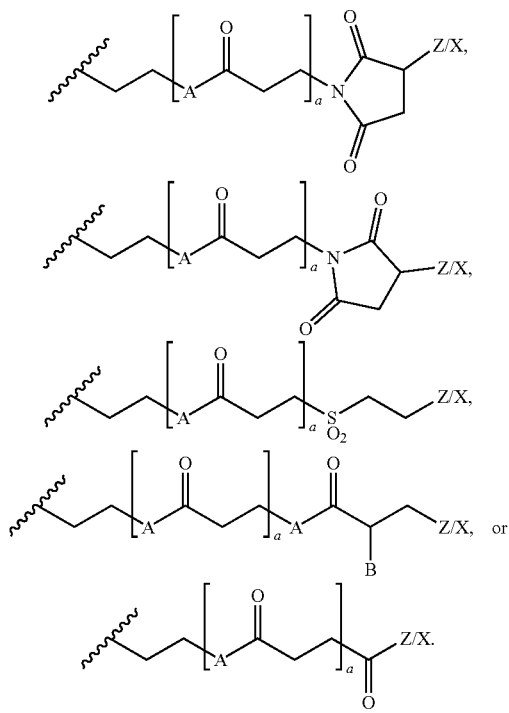

4. A method of repairing muscle tissue in a human patient in need thereof,
wherein the muscle tissue is diaphragm muscle tissue;
wherein the patient has muscular dystrophy; comprising forming micropunctures on the muscle tissue with a substrate comprising microneedles and forming a hydrogel matrix in vivo on the muscle tissue having micropunctures, wherein the hydrogel matrix is formed in vivo by applying to the muscle tissue having micropunctures:
a) a composition comprising a hydrophilic polymer conjugated to a plurality of adhesion peptides, wherein the hydrophilic polymer has the general formula:

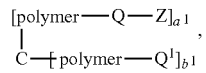

wherein 'polymer' represents polyethylene glycol, C represents a core, Q represents a linker, Z represents an adhesion peptide, wherein the adhesion peptide comprises the sequence GRGDSPC (SEQ ID NO: 1), CRGDS (SEQ ID NO: 2), CRGDSP (SEQ ID NO: 3), CPHSRN (SEQ ID NO: 4), CGWGGRGDSP (SEQ ID NO: 5), CGGSIDQVEPYSSTAQ (SEQ ID NO: 6), CGGRNIAEIIKDI (SEQ ID NO: 7), CGGDITYVRLKF (SEQ ID NO: 8), CGGDITVTLNRL (SEQ ID NO: 9), CGGRYVVLPR (SEQ ID NO: 10), CGGKAFDITYVRLKF (SEQ ID NO: 11), CGGEGYGEGYIGSR (SEQ ID NO: 12), CGGATLQLQEGRLHFXFDLGKGR, wherein X=Nle (SEQ ID NO: 13), CGGSYWYRIEASRTG (SEQ ID NO: 14), CGGGEFYFDLRLKGDKY (SEQ ID NO: 15), CKGGNGEPRGDTYRAY (SEQ ID NO: 16), CKGGPQVTRGDVFTMP (SEO ID NO: 17), CGGNRWHSIYITRFG (SEO ID NO: 18), CGGASIKVAVSADR (SEQ ID NO: 19), CGGTTVKYIFR (SEQ ID NO: 20), CGGSIKIRGTYS (SEQ ID NO: 21), CGGSINNNR (SEQ ID NO: 22), CGGSDPGYIGSR (SEQ ID NO: 23), CYIGSR (SEQ ID NO: 24), CGGTPGPQGIAGQGVV (SEQ ID NO: 25), CGGTPGPQGIAGQRVV (SEQ ID NO: 26), CGGMNYYSNS (SEQ ID NO: 27), CGGKKQRFRHRNRKG (SEQ ID NO: 28), CRGDGGGGGGGGGGGGPHSRN (SEQ ID NO: 29), CPHSRNSGSGSGSGSGRGD (SEQ ID NO: 30), Acetylated-GCYGRGDSPG (SEQ ID NO: 31), ((GPP)5GPC) (SEQ ID NO: 32), CRDGS (SEQ ID NO: 33), cyclic RGD{Fd}C (SEQ ID NO: 34), CGGRKRLQVQLSIRT (SEQ ID NO: 35), CIKVAV (SEQ ID NO: 36), CGGAASIKVAVSADR (SEQ ID NO: 37), CGGKRTGQYKL (SEQ ID NO: 38), CGGTYRSRKY (SEQ ID NO: 39), CGGYGGGP(GPP)5GFOGERPP(GPP)4GPC (SEQ ID NO: 40), CGGKRTGQYKLGSKTGPGQK (SEQ ID NO: 41), QAKHKQRKRLKSSC (SEQ ID NO: 42), SPKHHSQRARKKKNKNC (SEQ ID NO: 43), CGGXBBXBX, wherein B=basic residue and X=hydropathic residue (SEQ ID NO: 44), and CGGXBBBXXBX, wherein B=basic residue and X=hydropathic residue (SEQ ID NO: 45), or a combination thereof,
and
b) a composition comprising a crosslinker;
wherein at least one of the composition comprising the hydrophilic polymer and the composition comprising the crosslinker comprises a pro-myogenic agent,
wherein C represents a group having the formula:

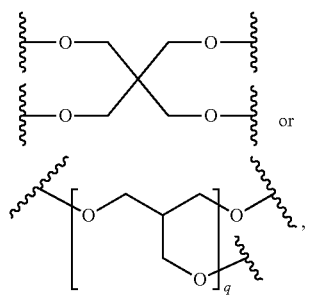

wherein q is from 1-6;
wherein the pro-myogenic agent comprises muscle stem cells and/or satellite cells, wherein the pro-myogenic agent further comprises a pro-myogenic protein comprising Wnt7a, FGF2, VEGF, IGF-1, GDNF, MG53, or a combination thereof;

$Q^1$ represents a group having the formula:

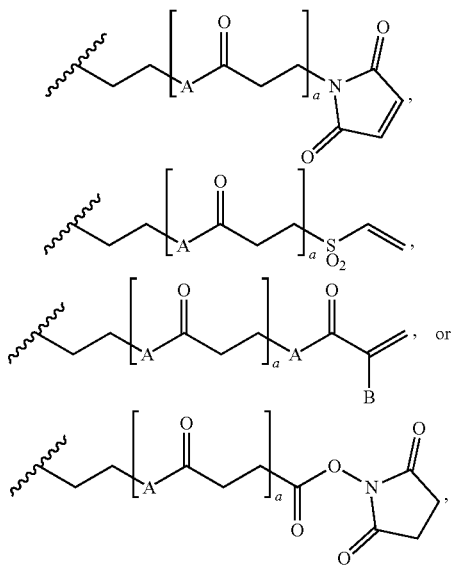

wherein A is independently selected from O or NH, a is independently selected from 0 or 1, B is selected from hydrogen or methyl, and ⸹ represents a link to a polyethylene glycol; and the crosslinker comprises 1,4-dithiothreitol poly(ethylene glycol) dithiol or a peptide having the sequence GCRDGPQG↓IWGQDRCG (SEQ ID NO: 46), GCRDGPQG↓IAGQDRCG (SEQ ID NO: 47), GCRDVPMS↓MRGGDRCG (SEQ ID NO: 48), GCR-DIPVS↓LRSGDRCG (SEQ ID NO: 49), GCRDRPFS↓MIMGDRCG (SEQ ID NO: 50), GCRDVPLS↓LTMGDRCG (SEQ ID NO: 51), GCRDVPLS↓LYSGDRCG (SEQ ID NO: 52), GCR-DIPES↓LRAGDRCG (SEQ ID NO: 53), GCRDSGESPAY↓YTADRCG (SEQ ID NO: 54), GCRDGGYAE↓LRMGGDRCG (SEQ ID NO: 55), GCRDGGPLG↓LYAGGDRCG (SEQ ID NO: 56), GCRDGPLG↓LWARDRCG (SEQ ID NO: 57), or a combination thereof.

5. The method according to claim 1, wherein the composition comprises muscle stem cells and/or satellite cells in an amount from 0.2-10×10³ cell/μL gel.

6. The method according to claim 5, wherein the composition comprises the pro-myogenic protein in an amount from 1-1,000 ng/μL gel.

7. The method according to claim 1, wherein the patient has Duchenne muscular dystrophy.

8. The method according to claim 1, wherein the patient has Duchenne-type muscular dystrophy, Becker muscular dystrophy, myotonic muscular dystrophy, facioscapulohumeral muscular dystrophy, congenital muscular dystrophy, or limb-girdle muscular dystrophy.

9. The method according to claim 1, wherein the patient is a pediatric patient.

10. The method according to claim 1, wherein the microneedles have an effective length of from 50-500 μm.

11. The method according to claim 1, wherein the muscle tissue is diaphragm muscle tissue.

12. The method according to claim 4, wherein the patient has Duchenne muscular dystrophy.

13. The method according to claim 4, wherein the patient has Duchenne-type muscular dystrophy, Becker muscular dystrophy, myotonic muscular dystrophy, facioscapulohumeral muscular dystrophy, congenital muscular dystrophy, or limb-girdle muscular dystrophy.

14. The method according to claim 4, wherein the patient is a pediatric patient.

15. The method according to claim 4, wherein the microneedles have an effective length of from 50-500 μm.

16. The method according to claim 4, wherein the muscle tissue is diaphragm muscle tissue.

17. The method according to claim 4, wherein C represents a group having the formula:

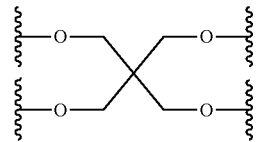 [SMILES: *OCC(CO*)(CO*)CO*]

$Q^1$ has the formula:

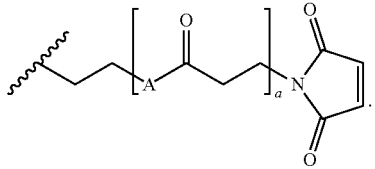

18. The method according to claim 1, wherein the adhesion peptide comprises the sequence GRGDSPC (SEQ ID NO: 1), CGGKAFDITYVRLKF SEQ ID NO: 11), CGG-EGYGEGYIGSR (SEQ ID NO: 12), or a combination thereof.

19. The method according to claim 1, wherein the crosslinker comprises a peptide having the sequence GCRDVPMS↓MRGGDRCG (SEQ ID NO: 48), GCRDVPLS↓LTMGDRCG (SEQ ID NO: 51), GCRDVPLS↓LYSGDRCG (SEQ ID NO: 52), or a combination thereof.

* * * * *

UNITED STATES PATENT AND TRADEMARK OFFICE
CERTIFICATE OF CORRECTION

Page 1 of 2

PATENT NO. : 12,397,084 B2
APPLICATION NO. : 17/263021
DATED : August 26, 2025
INVENTOR(S) : Woojin Han, Andres J. Garcia and Young C. Jang It is certified that error appears in the above-identified patent and that said Letters Patent is hereby corrected as shown below:

In the Claims

Column 56, Line 31, Claim 1 reading:
CGGTPGPQG (SEQ ID NO: 25), CGGMNYYSNS
Should read:
CGGTPGPQGIAGQGVV (SEQ ID NO: 25), CGGMNYYSNS Column 56, Line 33, Claim 1 reading:
(SEQ ID NO: 27), CGGKKQRFRHRNRKG (SE ID
Should read:
(SEQ ID NO: 27), CGGKKQRFRHRNRKG (SEQ ID Column 56, Lines 37-38, Claim 1 reading:
NO: 30), Acetylated-GCYGRGDSPG (SEO ID NO:
31), ((GPP)5GPC) (SEQ ID NO: 32), CRDGS (SEX ID
Should read:
NO: 30), Acetylated-GCYGRGDSPG (SEQ ID NO:
31), ((GPP)5GPC) (SEQ ID NO: 32), CRDGS (SEQ ID Column 56, Line 40, Claim 1 reading:
CGGRKRLOVOLSIRT (SEQ ID NO: 35), CIKVAV
Should read:
CGGRKRLQVQLSIRT (SEQ ID NO: 35), CIKVAV Column 56, Lines 46-47, Claim 1 reading:
QAKH KQRKRLKSSC (SEQ ID NO: 42), SPKH
HSQRARKKKNKNC (SEQ ID NO: 43), Signed and Sealed this
Ninth Day of December, 2025

John A. Squires
*Director of the United States Patent and Trademark Office*

Should read:
QAKHKQRKRLKSSC (SEQ ID NO: 42),
SPKHHSQRARKKKNKNC (SEQ ID NO: 43),

Column 56, Lines 58-59, Claim 1 reading:
GCRDRPFS↓MIMGDRCG (SEO ID NO: 50),
GCRDRPLS↓LTMGDRCG (SEO ID NO: 51),
Should read:
GCRDRPFS↓MIMGDRCG (SEQ ID NO: 50),
GCRDRPLS↓LTMGDRCG (SEQ ID NO: 51), Column 58, Lines 14-15, Claim 4 reading:
CKGGPQVTRGDVFTMP (SEO ID NO: 17), CGG-NRWHSIYITRFG (SEO ID NO: 18), CGGASIKVA-
Should read:
CKGGPQVTRGDVFTMP (SEQ ID NO: 17), CGG-NRWHSIYITRFG (SEQ ID NO: 18), CGGASIKVA- Column 60, Lines 26-32, Claim 17 reading:

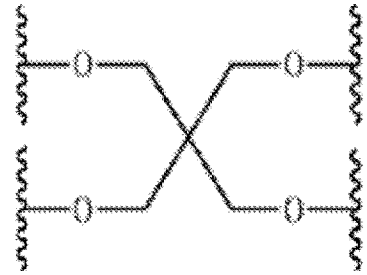

Should read:

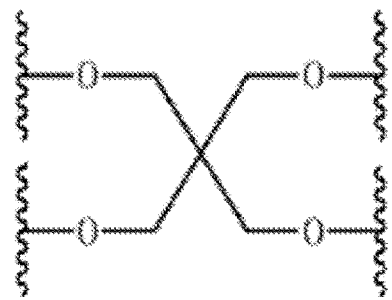

and

SEQUENCE LISTING

```
<160> NUMBER OF SEQ ID NOS: 60

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1

Gly Arg Gly Asp Ser Pro Cys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Cys Arg Gly Asp Ser Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct

<400> SEQUENCE: 4

Cys Pro His Ser Arg Asn
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Cys Gly Trp Gly Gly Arg Gly Asp Ser Pro
1               5                   10
```

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

Cys Gly Gly Ser Ile Asp Gln Val Glu Pro Tyr Ser Ser Thr Ala Gln
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic construct

<400> SEQUENCE: 7

Cys Gly Gly Arg Asn Ile Ala Glu Ile Ile Lys Asp Ile
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic construct

<400> SEQUENCE: 8

Cys Gly Gly Asp Ile Thr Tyr Val Arg Leu Lys Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Cys Gly Gly Asp Ile Thr Val Thr Leu Asn Arg Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

Cys Gly Gly Arg Tyr Val Val Leu Pro Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Cys Gly Gly Lys Ala Phe Asp Ile Thr Tyr Val Arg Leu Lys Phe
1               5                   10                  15

```
<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Cys Gly Gly Glu Gly Tyr Gly Glu Gly Tyr Ile Gly Ser Arg
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (16)..(16)
<223> OTHER INFORMATION: Xaa can be any naturally occurring amino acid

<400> SEQUENCE: 13

Cys Gly Gly Ala Thr Leu Gln Leu Gln Glu Gly Arg Leu His Phe Xaa
1               5                   10                  15

Phe Asp Leu Gly Lys Gly Arg
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic construct

<400> SEQUENCE: 14

Cys Gly Gly Ser Tyr Trp Tyr Arg Ile Glu Ala Ser Arg Thr Gly
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Cys Gly Gly Gly Glu Phe Tyr Phe Asp Leu Arg Leu Lys Gly Asp Lys
1               5                   10                  15

Tyr

<210> SEQ ID NO 16
<211> LENGTH: 16
<212> TYPE: PRT
<213> ORGANISM: Artificial Sequence
<220> FEATURE:
<223> OTHER INFORMATION: Synthetic construct

<400> SEQUENCE: 16

Cys Lys Gly Gly Asn Gly Glu Pro Arg Gly Asp Thr Tyr Arg Ala Tyr
1               5                   10                  15

<210> SEQ ID NO 17
<211> LENGTH: 16
<212> TYPE: PRT
<213> ORGANISM: Artificial Sequence
<220> FEATURE:
```

```
<223> OTHER INFORMATION: Synthetic construct

<400> SEQUENCE: 17

Cys Lys Gly Gly Pro Gln Val Thr Arg Gly Asp Val Phe Thr Met Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Cys Gly Gly Asn Arg Trp His Ser Ile Tyr Ile Thr Arg Phe Gly
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic construct

<400> SEQUENCE: 19

Cys Gly Gly Ala Ser Ile Lys Val Ala Val Ser Ala Asp Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct

<400> SEQUENCE: 20

Cys Gly Gly Thr Thr Val Lys Tyr Ile Phe Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic construct

<400> SEQUENCE: 21

Cys Gly Gly Ser Ile Lys Ile Arg Gly Thr Tyr Ser
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic construct

<400> SEQUENCE: 22

Cys Gly Gly Ser Ile Asn Asn Asn Arg
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic construct
```

<400> SEQUENCE: 23

Cys Gly Gly Ser Asp Pro Gly Tyr Ile Gly Ser Arg
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Synthetic construct

<400> SEQUENCE: 24

Cys Tyr Ile Gly Ser Arg
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic construct

<400> SEQUENCE: 25

Cys Gly Gly Thr Pro Gly Pro Gln Gly Ile Ala Gly Gln Gly Val Val
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Cys Gly Gly Thr Pro Gly Pro Gln Gly Ile Ala Gly Gln Arg Val Val
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Cys Gly Gly Met Asn Tyr Tyr Ser Asn Ser
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic construct

<400> SEQUENCE: 28

Cys Gly Gly Lys Lys Gln Arg Phe Arg His Arg Asn Arg Lys Gly
1               5                   10                  15

<210> SEQ ID NO 29
<211> LENGTH: 22
<212> TYPE: PRT
<213> ORGANISM: Artificial Sequence
<220> FEATURE:
<223> OTHER INFORMATION: Synthetic construct

```
<400> SEQUENCE: 29

Cys Arg Gly Asp Gly Gly Gly Gly Gly Gly Gly Gly Gly Gly
1               5                   10                  15

Gly Pro His Ser Arg Asn
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic construct

<400> SEQUENCE: 30

Cys Pro His Ser Arg Asn Ser Gly Ser Gly Ser Gly Ser Gly
1               5                   10                  15

Arg Gly Asp

<210> SEQ ID NO 31
<211> LENGTH: 20
<212> TYPE: PRT
<213> ORGANISM: Artificial Sequence
<220> FEATURE:
<223> OTHER INFORMATION: Synthetic construct

<400> SEQUENCE: 31

Ala Cys Glu Thr Tyr Leu Ala Thr Glu Asp Gly Cys Tyr Gly Arg Gly
1               5                   10                  15

Asp Ser Pro Gly
            20

<210> SEQ ID NO 32
<211> LENGTH: 18
<212> TYPE: PRT
<213> ORGANISM: Artificial Sequence
<220> FEATURE:
<223> OTHER INFORMATION: Synthetic construct

<400> SEQUENCE: 32

Gly Pro Pro Gly Pro Pro Gly Pro Pro Gly Pro Pro Gly Pro Pro Gly
1               5                   10                  15

Pro Cys

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Cys Arg Asp Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic construct

<400> SEQUENCE: 34

Cys Tyr Cys Leu Ile Cys Arg Gly Asp Phe Asp Cys
1               5                   10
```

<210> SEQ ID NO 35
<211> LENGTH: 15
<212> TYPE: PRT
<213> ORGANISM: Artificial Sequence
<220> FEATURE:
<223> OTHER INFORMATION: Synthetic construct

<400> SEQUENCE: 35

Cys Gly Gly Arg Lys Arg Leu Gln Val Gln Leu Ser Ile Arg Thr
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: Synthetic construct

<400> SEQUENCE: 36

Cys Ile Lys Val Ala Val
1               5

<210> SEQ ID NO 37
<211> LENGTH: 15
<212> TYPE: PRT
<213> ORGANISM: Artificial Sequence
<220> FEATURE:
<223> OTHER INFORMATION: Synthetic construct

<400> SEQUENCE: 37

Cys Gly Gly Ala Ala Ser Ile Lys Val Ala Val Ser Ala Asp Arg
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Cys Gly Gly Lys Arg Thr Gly Gln Tyr Lys Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct

<400> SEQUENCE: 39

Cys Gly Gly Thr Tyr Arg Ser Arg Lys Tyr
1               5                   10

<210> SEQ ID NO 40
<211> LENGTH: 46
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(26)
<223> OTHER INFORMATION: Xaa is hydroxyproline

<400> SEQUENCE: 40

Cys Gly Gly Tyr Gly Gly Gly Pro Gly Pro Pro Gly Pro Pro Gly Pro
1               5                   10                  15

Pro Gly Pro Pro Gly Pro Pro Gly Phe Xaa Gly Glu Arg Pro Pro Gly
            20                  25                  30

Pro Pro Gly Pro Pro Gly Pro Pro Gly Pro Pro Gly Pro Cys
        35                  40                  45

<210> SEQ ID NO 41
<211> LENGTH: 20
<212> TYPE: PRT
<213> ORGANISM: Artificial Sequence
<220> FEATURE:
<223> OTHER INFORMATION: Synthetic construct

<400> SEQUENCE: 41

Cys Gly Gly Lys Arg Thr Gly Gln Tyr Lys Leu Gly Ser Lys Thr Gly
1               5                   10                  15

Pro Gly Gln Lys
            20

<210> SEQ ID NO 42
<211> LENGTH: 14
<212> TYPE: PRT
<213> ORGANISM: Artificial Sequence
<220> FEATURE:
<223> OTHER INFORMATION: Synthetic construct

<400> SEQUENCE: 42

Gln Ala Lys His Lys Gln Arg Lys Arg Leu Lys Ser Ser Cys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Synthetic construct

<400> SEQUENCE: 43

Ser Pro Lys His His Ser Gln Arg Ala Arg Lys Lys Lys Asn Lys Asn
1               5                   10                  15

Cys

<210> SEQ ID NO 44
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be Iso, Val, Leu, Phe, Cys, Gly, Met,
      or Ala
<220> FEATURE:
<221> NAME/KEY: misc_feature
<222> LOCATION: (5)..(6)
<223> OTHER INFORMATION: Xaa can be Lys, Arg, or His
<220> FEATURE:
<221> NAME/KEY: misc_feature
<222> LOCATION: (7)..(7)
<223> OTHER INFORMATION: Xaa can be Iso, Val, Leu, Phe, Cys, Gly, Met,
      or Ala
<220> FEATURE:
<221> NAME/KEY: misc_feature
<222> LOCATION: (8)..(8)
<223> OTHER INFORMATION: Xaa can be Lys, Arg, or His

```
<220> FEATURE:
<221> NAME/KEY: misc_feature
<222> LOCATION: (9)..(9)
<223> OTHER INFORMATION: Xaa can be Iso, Val, Leu, Phe, Cys, Gly, Met,
      or Ala

<400> SEQUENCE: 44

Cys Gly Gly Xaa Xaa Xaa Xaa Xaa Xaa
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be Iso, Val, Leu, Phe, Cys, Gly, Met,
      or Ala
<220> FEATURE:
<221> NAME/KEY: misc_feature
<222> LOCATION: (5)..(7)
<223> OTHER INFORMATION: Xaa can be Lys, Arg, or His
<220> FEATURE:
<221> NAME/KEY: misc_feature
<222> LOCATION: (8)..(9)
<223> OTHER INFORMATION: Xaa can be Iso, Val, Leu, Phe, Cys, Gly, Met,
      or Ala
<220> FEATURE:
<221> NAME/KEY: misc_feature
<222> LOCATION: (10)..(10)
<223> OTHER INFORMATION: Xaa can be Lys, Arg, or His
<220> FEATURE:
<221> NAME/KEY: misc_feature
<222> LOCATION: (11)..(11)
<223> OTHER INFORMATION: Xaa can be Iso, Val, Leu, Phe, Cys, Gly, Met,
      or Ala

<400> SEQUENCE: 45

Cys Gly Gly Xaa Xaa Xaa Xaa Xaa Xaa Xaa Xaa
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Synthetic construct

<400> SEQUENCE: 46

Gly Cys Arg Asp Gly Pro Gln Gly Ile Trp Gly Gln Asp Arg Cys Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic construct

<400> SEQUENCE: 47

Gly Cys Arg Asp Gly Pro Gln Gly Ile Ala Gly Gln Asp Arg Cys Gly
1               5                   10                  15

<210> SEQ ID NO 48
<211> LENGTH: 16
<212> TYPE: PRT
<213> ORGANISM: Artificial Sequence
<220> FEATURE:
```

<223> OTHER INFORMATION: Synthetic construct

<400> SEQUENCE: 48

Gly Cys Arg Asp Val Pro Met Ser Met Arg Gly Gly Asp Arg Cys Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

Gly Cys Arg Asp Ile Pro Val Ser Leu Arg Ser Gly Asp Arg Cys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic construct

<400> SEQUENCE: 50

Gly Cys Arg Asp Arg Pro Phe Ser Met Ile Met Gly Asp Arg Cys Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic construct

<400> SEQUENCE: 51

Gly Cys Arg Asp Val Pro Leu Ser Leu Thr Met Gly Asp Arg Cys Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic construct

<400> SEQUENCE: 52

Gly Cys Arg Asp Val Pro Leu Ser Leu Tyr Ser Gly Asp Arg Cys Gly
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic construct

<400> SEQUENCE: 53

Gly Cys Arg Asp Ile Pro Glu Ser Leu Arg Ala Gly Asp Arg Cys Gly
1               5                   10                  15

<210> SEQ ID NO 54
<211> LENGTH: 18
<212> TYPE: PRT
<213> ORGANISM: Artificial Sequence
<220> FEATURE:
<223> OTHER INFORMATION: Synthetic construct -continued

<400> SEQUENCE: 54

Gly Cys Arg Asp Ser Gly Glu Ser Pro Ala Tyr Tyr Thr Ala Asp Arg
1               5                   10                  15

Cys Gly

<210> SEQ ID NO 55
<211> LENGTH: 18
<212> TYPE: PRT
<213> ORGANISM: Artificial Sequence
<220> FEATURE:
<223> OTHER INFORMATION: Synthetic construct

<400> SEQUENCE: 55

Gly Cys Arg Asp Gly Gly Tyr Ala Glu Leu Arg Met Gly Gly Asp Arg
1               5                   10                  15

Cys Gly

<210> SEQ ID NO 56
<211> LENGTH: 18
<212> TYPE: PRT
<213> ORGANISM: Artificial Sequence
<220> FEATURE:
<223> OTHER INFORMATION: Synthetic construct

<400> SEQUENCE: 56

Gly Cys Arg Asp Gly Gly Pro Leu Gly Leu Tyr Ala Gly Gly Asp Arg
1               5                   10                  15

Cys Gly

<210> SEQ ID NO 57
<211> LENGTH: 16
<212> TYPE: PRT
<213> ORGANISM: Artificial Sequence
<220> FEATURE:
<223> OTHER INFORMATION: Synthetic construct

<400> SEQUENCE: 57

Gly Cys Arg Asp Gly Pro Leu Gly Leu Trp Ala Arg Asp Arg Cys Gly
1               5                   10                  15

<210> SEQ ID NO 58
<211> LENGTH: 246
<212> TYPE: PRT
<213> ORGANISM: Bacillus sphaericus

<400> SEQUENCE: 58

Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Pro Thr Ala
            115                 120                 125

Gln Asp Pro Met Pro Phe Leu Lys Ser Ala Gly Tyr Gly Lys Ala Gly
        130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245

<210> SEQ ID NO 59
<211> LENGTH: 45
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: Xaa is hydroxyproline

<400> SEQUENCE: 59

Gly Gly Tyr Gly Gly Pro Gly Pro Pro Gly Pro Pro Gly Pro Pro Gly
1               5                   10                  15

Pro Pro Gly Pro Pro Gly Phe Xaa Gly Glu Arg Gly Pro Pro Gly Pro
            20                  25                  30

Pro Gly Pro Pro Gly Pro Pro Gly Pro Pro Gly Pro Cys
        35                  40                  45

<210> SEQ ID NO 60
<211> LENGTH: 16
<212> TYPE: PRT
<213> ORGANISM: Artificial Sequence
<220> FEATURE:
<223> OTHER INFORMATION: Synthetic construct

<400> SEQUENCE: 60

Gly Cys Arg Asp Val Pro Met Ser Met Arg Gly Gly Asp Arg Cys Gly
1               5                   10                  15